(12) United States Patent
Varum et al.

(10) Patent No.: US 12,370,146 B2
(45) Date of Patent: Jul. 29, 2025

(54) METHOD OF PRODUCING A DELAYED RELEASE DRUG FORMULATION

(71) Applicant: Tillotts Pharma AG, Rheinfelden (CH)

(72) Inventors: Felipe Varum, Rheinfelden (CH);
Laetitia Von Rochow, Rheinfelden (CH); Carsten Markus Füller, Rheinfelden (CH); Roberto Carlos Bravo González, Rheinfelden (CH)

(73) Assignee: Tillotts Pharma AG, Rheinfelden (CH)

( * ) Notice: Subject to any disclaimer, the term of this patent is extended or adjusted under 35 U.S.C. 154(b) by 161 days.

(21) Appl. No.: 17/309,554

(22) PCT Filed: Dec. 5, 2019

(86) PCT No.: PCT/EP2019/083910
§ 371 (c)(1),
(2) Date: Jun. 4, 2021

(87) PCT Pub. No.: WO2020/115255
PCT Pub. Date: Jun. 11, 2020

(65) Prior Publication Data
US 2022/0023222 A1    Jan. 27, 2022

(30) Foreign Application Priority Data

Dec. 7, 2018 (EP) .................................... 18211152

(51) Int. Cl.
| A61K 9/16 | (2006.01) |
| A61K 9/00 | (2006.01) |
| A61K 9/20 | (2006.01) |
| A61K 9/28 | (2006.01) |

(52) U.S. Cl.
CPC .......... *A61K 9/2893* (2013.01); *A61K 9/0053* (2013.01); *A61K 9/2013* (2013.01); *A61K 9/2054* (2013.01); *A61K 9/2059* (2013.01); *A61K 9/2095* (2013.01); *A61K 9/2846* (2013.01); *A61K 9/286* (2013.01); *A61K 9/2886* (2013.01)

(58) Field of Classification Search
CPC .......... A61K 9/14; A61K 9/16; A61K 9/1605; A61K 9/1611; A61K 9/1623; A61K 9/1629; A61K 9/1647; A61K 9/167; A61K 9/1682; A61K 9/1688
See application file for complete search history.

(56) References Cited

U.S. PATENT DOCUMENTS

| 5,422,121 | A | 6/1995 | Lehmann et al. |
| 9,364,440 | B2 | 6/2016 | Bravo Gonzalez et al. |
| 9,814,681 | B2 | 11/2017 | Oliveira Varum et al. |
| 10,272,048 | B2 | 4/2019 | Oliveira Varum et al. |
| 10,799,515 | B2 | 10/2020 | Varum et al. |
| 11,517,534 | B2 | 12/2022 | Oliveira Varum et al. |
| 11,534,406 | B2 | 12/2022 | Oliveira Varum et al. |
| 2006/0210631 | A1 | 9/2006 | Patel et al. |
| 2007/0243223 | A1 | 10/2007 | Alasri et al. |
| 2007/0243253 | A1* | 10/2007 | Basit .................... A61K 31/573 514/159 |
| 2008/0200482 | A1 | 8/2008 | Petereit et al. |
| 2009/0208574 | A1 | 8/2009 | Chen |
| 2015/0125525 | A1* | 5/2015 | Bravo Gonzalez .... A61K 9/288 427/2.21 |
| 2016/0250232 | A1 | 9/2016 | Varum et al. |
| 2019/0336449 | A1 | 11/2019 | Varum et al. |
| 2022/0016037 | A1 | 1/2022 | Varum et al. |
| 2022/0016038 | A1 | 1/2022 | Varum et al. |

FOREIGN PATENT DOCUMENTS

| AU | 2012 247 013 | 11/2012 | |
| CN | 1239425 | 12/1999 | |
| CN | 101448488 | 6/2009 | |
| CN | 104271113 | 1/2015 | |
| CN | 105412904 | 3/2016 | |
| CN | 105555260 | 5/2016 | |
| CN | 105832691 | 8/2016 | |
| EP | 0 343 993 | 11/1989 | |
| EP | 0 502 032 | 9/1992 | |
| EP | 0 673 645 | 9/1995 | |
| EP | 3 257 501 | 12/2017 | |
| EP | 3257501 A1 * | 12/2017 | ......... A61K 31/4164 |
| EP | 3 278 792 | 2/2018 | |

(Continued)

OTHER PUBLICATIONS

Chinese Office Action dated Jun. 27, 2022 in Chinese Application No. 201980081115.9, with English translation, 20 pages.

Akhgari et al, "Permeability and swelling studies on free films containing inulin in combination with different polymethacrylates aimed for colonic drug delivery", European Journal of Pharmaceutical Sciences, vol. 28, Mar. 2006, pp. 307-314.

Milojevic et al., "Amylose as a coating for drug delivery to the colon: Preparation and in vitro evaluation using 5-aminosalicylic acid pellets", Journal of Controlled Release, vol. 38, 1996, pp. 75-84.

Chilean Office Action dated May 16, 2023, in Chilean Patent Application No. 202101472, with English translation, 32 pages.

Chinese Office Action dated Jan. 19, 2023, in Chinese Patent Application No. 201980081115.9, with English translation, 22 pages.

(Continued)

*Primary Examiner* — Micah Paul Young
(74) *Attorney, Agent, or Firm* — Grüneberg and Myers PLLC (57) ABSTRACT

A method produces a coatable core for a delayed release drug formulation for oral administration, to deliver a drug to the colon. The method involves forming a core containing a drug. An outer layer coating preparation is formed by combining a first aqueous preparation of an enzymatically degradable polymer, which is degradable by colonic bacterial enzymes; a second aqueous preparation of a film-forming enteric polymer having a pH threshold of about pH 6 or above; and an organic anti-tack agent. The core is then coated with the outer layer coating preparation to form an outer layer coated core.

20 Claims, 3 Drawing Sheets

(56) References Cited

FOREIGN PATENT DOCUMENTS

| | | | | |
|---|---|---|---|---|
| GB | 2367002 | 3/2002 | | |
| JP | 2015-515964 | 6/2015 | | |
| JP | 2016-535030 | 11/2016 | | |
| JP | 2017-145267 | 8/2017 | | |
| JP | 2019-518758 | 7/2019 | | |
| JP | 2020-530006 | 10/2020 | | |
| KR | 10-2015-0004910 | 1/2015 | | |
| TW | 201542243 | 11/2015 | | |
| WO | 91/07949 | 6/1991 | | |
| WO | 96/36321 | 11/1996 | | |
| WO | WO-9636321 A1 * | 11/1996 | ............ | A61K 31/44 |
| WO | 98/16206 | 4/1998 | | |
| WO | 99/21536 | 5/1999 | | |
| WO | 99/25325 | 5/1999 | | |
| WO | 01/76562 | 10/2001 | | |
| WO | 03/068196 | 8/2003 | | |
| WO | 2004/052339 | 6/2004 | | |
| WO | WO2007/122374 | 11/2007 | | |
| WO | 2008/135090 | 11/2008 | | |
| WO | 2012/129551 | 9/2012 | | |
| WO | 2013/164315 | 11/2013 | | |
| WO | 2013/164316 | 11/2013 | | |
| WO | 2015/062640 | 5/2015 | | |
| WO | WO-2015062640 A1 * | 5/2015 | ............ | A61J 3/005 |
| WO | 2017/138877 | 8/2017 | | |
| WO | 2018/005606 | 1/2018 | | |
| WO | 2019/032027 | 2/2019 | | |
| WO | 2020/115254 | 6/2020 | | |

OTHER PUBLICATIONS

Eurasian Office Action dated Jun. 19, 2023, in Eurasian Patent Application No. 202191597/28, with English translation, 6 pages.
Eurasian Office Action dated Oct. 28, 2022, in Eurasian Patent Application No. 202191597/28, with English translation, 4 pages.
Georgian Office Action dated Feb. 20, 2023, in Georgian Patent Application No. AP 2019 15683, with English translation, 6 pages.
Georgian Office Action dated Nov. 26, 2021, in Georgian Patent Application No. AP 2019 15683, with English translation, 4 pages.
Georgian Office Action dated Oct. 25, 2022, in Georgian Patent Application No. AP 2019 15683, with English translation, 8 pages.
Indian Office Action dated Oct. 11, 2022, in Indian Patent Application No. 202127026904, 6 pages.
Indonesian Office Action dated Jan. 13, 2023, in Indonesian Patent Application No. P00202105184, with English translation, 6 pages.
Japanese Office Action dated May 9, 2023, in Japanese Patent Application No. 2021-532824, with English translation, 5 pages.
Saudi Arabian Office Action dated Jun. 6, 2021, in Saudi Arabian Patent Application No. 521422199, with English translation, 11 pages.
Saudi Arabian Office Action dated Nov. 25, 2022, in Saudi Arabian Patent Application No. 521422199, with English translation, 8 pages.
Ukrainian Office Action dated Mar. 16, 2023, in Ukrainian Patent Application No. a 2021 03934, with English translation, 13 pages.
Ukrainian Office Action dated May 26, 2022, in Ukraine Patent Application No. a 2021 03934, with English translation, 10 pages.
International Search Report issued Mar. 3, 2020 in PCT/EP2019/083910.
Written Opinion issued Mar. 3, 2020 in PCT/EP2019/083910.
Japanese Office Action dated Jul. 29, 2022, in Japanese Patent Application No. 2021-532824, with English translation, 11 pages.
Chilean Office Action dated Aug. 18, 2022, in Chilean Patent Application No. 202101472, with English translation 28 pages.
Written Opinion dated Sep. 19, 2022, in Singapore Patent Application No. 11202105691R, 7 pages.
Japanese Decision to grant a patent received for Japanese Patent Application No. 2021-532824, dated Oct. 27, 2023, with English translation, 5 pages.

European Communication under Rule 71(3) EPC, Intention to grant received for European Patent Application No. 18211152.6, dated Oct. 13, 2023, 53 pages.
Chinese Office Action received for Chinese Patent Application No. 201980081115.9, dated Jun. 29, 2023, with English translation, 33 pages.
Colombian Office Action received for Colombian Patent Application No. NC2021/0008683, dated Dec. 28, 2023, 12 pages.
European Office Action received for European Patent Application No. 19816317.2, dated Sep. 11, 2023, 7 pages.
Mexican Office Action received for Mexico Patent Application No. MX/a/2021/006603, dated Oct. 6, 2023, with English translation, 14 pages.
Philippine Office Action received for Philippine Patent Application No. 1/2021/551292, dated Sep. 12, 2023, 5 pages.
Saudi Arabian Office Action received for Saudi Arabian Patent Application No. 521422199, dated Dec. 7, 2023, with English translation, 7 pages.
Saudi Arabian Office Action received for Saudi Arabian Patent Application No. 521422199, dated Jun. 9, 2023, with English translation, 8 pages.
Sri Lanka Office Action received for Sri Lanka Patent Application No. 21801, dated Oct. 9, 2023, 1 page.
Taiwanese Office Action received for Taiwanese Patent Application No. 108144379, dated Jan. 23, 2024, with English translation 11 pages.
Ukraine Office Action received for Ukraine Patent Application No. a 2021 03934, dated Sep. 13, 2023, with English translation, 12 pages.
United Arab Emirates Office Action with Search Report received for United Arab Emirates Patent Application No. P6000925/ 2021, mailed on Dec. 26, 2023, 8 pages.
Uzbekistan Office Action received for Uzbekistan Patent Application No. I AP20210356/9-son dated Sep. 13, 2023, with English Translation, 5 pages.
Vietnamese Office Action received for Vietnamese Patent Application No. 1-2021-03997, dated Nov. 22, 2023, with English Translation, 3 pages.
Bahrain Examination Fee Request dated May 26, 2024, in Bahrain Patent Application No. 20210131, 2 pages.
Costa Rican Examination Fee Request dated Mar. 4, 2024, in Costa Rica Patent Application No. 2021-0000366, 2 pages.
Brazilian First Examination Report dated Apr. 22, 2024, in Brazilian Patent Application No. BR112021010914-5, with English translation, 8 pages.
Canadian First Examination Report dated Apr. 5, 2024, in Canadian Patent Application No. 3,122,013, 3 pages.
Israeli First Examination dated Feb. 6, 2024, in Israeli Patent Application No. 283718, 4 pages.
Korean First Exam Report dated May 22, 2024, in Korean Patent Application No. 10-2021-7020595, with English translation, 12 pages.
Thailand First Examination Report dated Mar. 4, 2024, in Thailand Patent Application No. 2101003180, with English translation, 12 pages.
Indian Hearing Notice dated Feb. 19, 2024, in Indian Patent Application No. 202127026904, 4 pages.
Indian Intimation of Grant dated May 2, 2024, in Indian Patent Application No. 202127026904, 1 page.
Mexican Second Examination Report dated Apr. 24, 2024, in Mexican Patent Application No. MX/a/2021/006603, with English translation, 20 pages.
Philippine Second Exam Report dated Jan. 22, 2024, in Philippine Patent Application No. 1/2021/551292, 5 pages.
European Communication under Rule 71(3) EPC, second Intention to grant dated Apr. 2, 2024, in European Patent Application No. 18211152.6, 5 pages.
Singapore Second Written Opinion dated Apr. 22, 2024, in Singapore Patent Application No. 11202105691R, 5 pages.
Eurasian Third Examination Report dated Apr. 15, 2024, in Eurasian Patent Application No. 202191597/28, with English translation 8 pages.

(56) References Cited

OTHER PUBLICATIONS

Brazilian Office Action dated Nov. 1, 2023, in Brazilian Patent Application No. BR112021010915-3, 6 pages with English translation.
Brazilian Office Action dated Jan. 8, 2024, in Brazil Patent Application No. 112021010913-7, 4 pages.
Canadian Office Action dated Mar. 7, 2024, in Canadian Application No. 3,122,033, 5 pages.
Chilean Office Action received for Chilean Patent Application No. 202101445 mailed on Oct. 17, 2022, 18 pages.
Chinese Office Action dated Jun. 22, 2022, in Chinese Application No. 201980081059.9, 10 pages with English translation.
Chinese Office Action dated Jun. 24, 2022, in Chinese Application No. 201980081039.1, 9 pages with English translation.
Chinese Office Action dated Nov. 2, 2022, in Chinese Application No. 201980081039.1, 9 pages with English translation.
Chinese Office Action received for Chinese Application No. 201980081059.9 mailed on Nov. 16, 2022, 10 pages with English translation.
Chinese Rejection Decision dated Mar. 22, 2023, in Chinese Application No. 201980081039.1, 5 pages.
Chinese Decision of Rejection received for Chinese Application No. 201980081059.9 mailed on Mar. 23, 2023, 11 pages with English translation.
Colombian Office Action dated Aug. 23, 2023, in Colombian Patent Application No. NC2021/0008688, 14 pages with English translation.
English translation of Saudi Arabian First Substantive Examination Report dated Jul. 6, 2022, in Saudi Arabia Patent Application No. 521422194, 4 pages.
Eurasian Office Action dated Nov. 25, 2022, in Eurasian Patent Application No. 202191431/28, 6 pages with English translation.
Eurasian Office Action received for Eurasian Patent Application No. 202191574/28 mailed on Nov. 29, 2022, 5 pages.
Eurasian Office Action dated Jun. 22, 2023, in Eurasian Patent Application No. 202191431/28, 15 pages with English translation.
Eurasian Office Action dated Jun. 28, 2023, in Eurasian Patent Application No. 202191574/28, 14 pages with English translation.
European Communication pursuant to Article 94(3) EPC received for European Patent Application No. 18211154.2 mailed on Nov. 29, 2021, 11 pages.
European Communication under Rule 71(3) EPC: Intention to grant received for European Patent Application No. 18211154.2, dated Sep. 6, 2023, 54 pages.
European Communication pursuant to Article 94(3) EPC dated Mar. 21, 2024, in European Application No. 18211141.9, 5 pages.
Extended European Search Report dated Jun. 6, 2019, in European Application No. 18211141.9, 9 pages.
Extended European Search Report for European Application No. 1821154.2 mailed on Jul. 8, 2019, 10 pages.
Indian Office Action dated Oct. 10, 2022, in Indian Patent Application No. 202127024588, 5 pages.
Indian Office Action received for Indian Application No. 202127024589 mailed on Oct. 11, 2022, 6 pages.
Indonesian Office Action received for Indonesian Application No. P00202105182 mailed on Jan. 16, 2023, 3 pages.
International Search Report issued Feb. 20, 2020, in PCT/EP2019/083912, 6 pages.
International Search Report issued Mar. 5, 2020, in PCT/EP2019/083909, 5 pages.
Japanese Office Action dated Jun. 24, 2022, in Japanese Patent Application No. 2021-532415, 6 pages with English translation.
Japanese Office Action dated Jun. 24, 2022, in Japanese Patent Application No. 2021-532823, 8 pages with English translation.
Japanese Office Action dated Mar. 28, 2023, in Japanese Patent Application No. 2021-532415, 8 pages with English translation.
Japanese Office Action dated Mar. 28, 2023, in Japanese Patent Application No. 2021-532823, 12 pages with English translation.
Korean Office Action dated May 29, 2024, in Korean Application No. 10-2021-7020598, 11 pages with English translation.
Mexican Office Action dated Oct. 5, 2023, in Mexican Patent Application No. MX/a/2021/006693, 12 pages with English translation.
Taiwanese Office Action dated Mar. 31, 2023, in Taiwanese Patent Application No. 108144380, 21 pages with English translation.
Taiwanese Office Action dated May 24, 2023, in Taiwanese Patent Application No. 108144381, 15 pages with English translation.
Translation of Sri Lanka Office Action dated Oct. 9, 2023, in Sri Lanka Patent Application No. 21800, 1 page.
Translation of United Arab Emirates Office Action dated Dec. 27, 2023, in United Arab Emirates Patent Application No. P6000924/2021, 7 pages.
Ukraine Office Action received for Ukraine Patent Application No. a202103910, dated May 31, 2023, 9 pages with English translation.
United States Office Action received for U.S. Appl. No. 17/309,546, dated Jun. 24, 2024, 15 pages.
Uzbekistan first examination report dated Sep. 13, 2023, in Uzbekistan Patent Application No. 20210350/7-son, 3 pages.
Vietnamese Office Action dated Sep. 29, 2023, in Vietnamese Patent Application No. 1-2021-03963, 2 pages.
Written Opinion issued Feb. 20, 2020, in PCT/EP2019/083912, 6 pages.
Written Opinion issued Mar. 5, 2020, in PCT/EP2019/083909, 8 pages.
Written Opinion received for Singapore Application No. 11202105695W, mailed on Sep. 19, 2022, 6 pages.
U.S. Appl. No. 17/309,546, filed Jun. 4, 2021, 2022/0016038, Varum et al.
U.S. Appl. No. 17/309,558, filed Jun. 4, 2021, 2022/0016037, Varum et al.
Decision to grant a European patent pursuant to Article 97(1) EPC received for European Patent Application No. 18211152.6, mailed on Dec. 5, 2024, 2 pages.
Notice of Allowance received for Philippine Patent Application No. 1/2021/551292, mailed on Sep. 19, 2024, 3 pages.
Notice of Allowance received for Taiwanese Patent Application No. 108144379, mailed on Oct. 14, 2024, 4 pages with English translation.
Notice of Allowance received for Ukrainian Patent Application No. a 2021 03934, mailed on Aug. 2, 2024, 13 pages with English translation.
Office Action received for Australian Patent Application No. 2019392854, mailed on Jul. 18, 2024, 3 pages.
Office Action received for Colombian Patent Application No. NC2021/0008683, mailed on Jul. 12, 2024, 21 pages with English translation.
Office Action received for Costa Rican Patent Application No. 2021-0000366, mailed on Oct. 28, 2024, 6 pages.
Intention to Grant received for European Patent Application No. 18211152.6, mailed on Aug. 30, 2024, 52 pages.
Office Action received for Malaysian Patent Application No. PI2021003031, mailed on Nov. 13, 2024, 3 pages.
Office Action received for Mexican Patent Application No. MX/a/2021/006603, mailed on Aug. 14, 2024, 14 pages with English translation.
Office Action received for Philippine Patent Application No. 1/2021/551292, mailed on Jul. 1, 2024, 5 pages.
Office Action received for Vietnamese Patent Application No. 1-2021-03997, mailed on Jul. 31, 2024, 4 pages with English translation.
Office Action received for Vietnamese Patent Application No. 1-2021-03997, mailed on Nov. 27, 2024, 4 pages with English translation.
Office Action received for U.S. Appl. No. 17/309,546, mailed on Jan. 17, 2025, 18 pages.
Møller et al., "Structural biology of starch-degrading enzymes and their regulation", Current Opinion in Structural Biology, vol. 40, Jul. 21, 2016, pp. 1-27.
Office Action received for U.S. Appl. No. 17/309,558, mailed on Apr. 10, 2025, 28 pages.

* cited by examiner

METHOD OF PRODUCING A DELAYED RELEASE DRUG FORMULATION

CROSS-REFERENCE TO RELATED APPLICATIONS

This application is the National Stage entry under § 371 of International Application No. PCT/EP2019/083910, filed on Dec. 5, 2019, and which claims the benefit of priority to European Application No. 18211152.6, filed on Dec. 7, 2018. The content of each of these applications is hereby incorporated by reference in its entirety.

BACKGROUND OF THE INVENTION

Field of the Invention

The present invention relates to a method of producing a delayed release drug formulation with a core comprising a drug and a delayed release coating. In particular, it relates to a delayed release formulation for delivering a drug to the colon.

Description of Related Art

The targeting of drugs to the intestine is well known and has been known for over one hundred years. Commonly, the target of the drugs is the small intestine although the colon can be utilised as a means of achieving local therapy or systemic treatment. The requirements for the coatings on the drugs are different depending on the target site. In order to reach the colon, it is necessary for the drugs to pass through the small intestine, and therefore it is a requirement that a delayed release coating intended to release the drug in the colon does not release the drug in the small intestine.

Coated products for release in the small intestine commonly use polymer coatings which dissolve or disintegrate in a pH dependent manner. In the low pH environment of the stomach, the polymer coating is insoluble. However, on reaching the small intestine, the pH rises to 5 and above and the polymeric coating dissolves or disintegrates. A commonly used coating is one containing ionizable carboxylic groups. At higher pH levels, the carboxylic groups ionize, allowing the polymer coatings to disintegrate or dissolve. Common polymers of this type which are used include Eudragit® L and Eudragit® S.

Various methods of improving the release in the small intestine by ensuring an earlier release of the drug are known. US2008/0200482 is one of a number of references which discloses partially neutralizing the carboxylic groups in order to reduce the pH at which disintegration occurs. WO2008/135090 discloses a tablet with an inner coat of partially neutralized material and an outer coat with less or no neutralization. This is said to result in disintegration at an earlier time point when transferred from the stomach.

Release of drugs in the colon typically requires an alternative approach. The colon is susceptible to a number of disease states, including inflammatory bowel disease, irritable bowel syndrome, constipation, diarrhoea, infection and carcinoma. In such conditions, drug targeting to the colon would maximise the therapeutic effectiveness of the treatment. The colon can also be utilised as a portal for the entry of drugs into the systemic circulation. Various formulations have been developed for colonic drug delivery, including pro-drugs as well as formulated dosage forms, with the latter being more popular since the concept once proved can be applied to other drugs.

The high bacterial population of the colon has also been exploited in developing colonic drug delivery dosage forms through the use, as digestible carrier materials, of naturally occurring polysaccharides that constitute substrates for the numerous enzymes produced by the resident colonic bacteria. These materials are able to pass through the upper gastrointestinal regions intact but are digested upon entry into the colon. Examples include starch, amylose, amylopectin, pectin, chitosan, galactomannan and guar gum.

One major attraction of using polysaccharides in this bacterial enzyme approach to colonic drug delivery is that materials used are of food grade and so would be safe for use in humans. They are usually applied as coatings or incorporated in the core material as a matrix carrier, and their digestion on entry into the colon by the colonic bacterial enzymes leads to the release of the drug load. An example of such a formulation, which employs an amylose coating, is disclosed in EP0343993A (BTG International Limited).

A major limitation with these naturally occurring materials, however, is that they swell excessively in aqueous media leading to leaching of the drug load in the upper gastrointestinal regions. To circumvent this problem, the naturally occurring materials have been utilised in a mixture with various impermeable materials.

EP0502032A (British Technology Group Ltd) teaches the use of an outer coating comprising a film-forming cellulose or acrylate polymer material and amorphous amylose for a tablet comprising an active compound. The polymer material used is a pH independent release polymer material.

An article in Journal of Controlled Release (Milojevic et al; 38; (1996); 75-84) reports the results of investigations concerning the incorporation of a range of insoluble polymers into an amylose coating in order to control amylose swelling. A range of cellulose and acrylate based co-polymers are assessed, and a commercially available ethyl cellulose (Ethocel®) is found to control the swelling most effectively. A pH dependent soluble coating of Eudragit® L100 is employed but only in a multi-layer system comprising a bioactive coated with an inner coating of amylose and then an outer coating of Eudragit® L 100.

A further amylose-based coating composition is disclosed in WO99/21536A (BTG International Limited). The coating composition comprises a mixture of amylose and a water-insoluble pH independent film-forming polymer which is formed from a water-insoluble cellulosic or acrylate polymer material.

WO99/25325A (BTG International Limited) also discloses a delayed release coating comprising amylose and (preferably) ethyl cellulose or alternatively an insoluble acrylate polymer. The coating composition also includes a plasticiser and the method finds particular application in the preparation of dosage forms comprising active materials that are unstable at temperatures in excess of 60° C., as the composition is formed at lower temperatures than this.

WO03/068196A (Alizyme Therapeutics Ltd) discloses a specific delayed release coating for the bioactive prednisolone sodium metasulphobenzoate comprising glassy amylose, ethyl cellulose and dibutyl sebacate.

The use of polysaccharides other than amorphous amylose in a delayed release coating is disclosed in GB2367002 (British Sugar PLC). Examples include guar gum, karaya gum, gum tragacanth and xanthan gum. Microparticles of these polysaccharides are dispersed in a water-insoluble film-forming polymer matrix formed for example from a cellulose derivative, an acrylic polymer or a lignin.

WO01/76562A (Tampereen Patenttitoimisto Oy) discloses a peroral pharmaceutical formulation containing a drug and a chitosan (a polysaccharide obtained from chitin) for controlling its release. The drug and the chitosan are mixed into a homogeneous mechanical powder mixture which is granulated and then optionally tabletised. The granulation may be performed with an enteric polymer (such as a copolymer of methacrylic acid) or the granules may be provided with a porous enteric coating.

WO2004/052339A (Salvona LLC) discloses a pH dependent drug release system which is a free-flowing powder of solid hydrophobic nano-spheres comprising a drug encapsulated in a pH-sensitive micro-sphere. The nano-spheres are formed from the drug in combination with a wax material, and the pH-sensitive micro-sphere formed from a pH-sensitive polymer (such as a Eudragit® polymer) in combination with a water-sensitive material such as a polysaccharide.

An article in the European Journal of Pharmaceutical Sciences (Akhgari et al; 28; March 2006; 307-314) reports the results of investigations into the use of certain polymethacrylate polymers to, inter alia, control the swelling of inulin. The polymethacrylate polymers tested were Eudragit® RS; Eudragit® RL; 1:1 mixtures of Eudragit® RS and Eudragit® RL; Eudragit® FS; and 1:1 mixtures of Eudragit® RS and Eudragit® S.

U.S. Pat. No. 5,422,121 (Röhm GmbH) discloses an oral dosage form having a core containing at least one active ingredient enclosed within a shell material which comprises a polysaccharide that decomposes in the colon in admixture with a film-forming polymer. The ratio by weight of polysaccharide to film forming polymer is from 1:2 to 5:1, preferably from 1:1 to 4:1. Premature diffusion of the active ingredient from the core can be suppressed using a gastric resistant isolating layer. The reference exemplifies inter alia tablets having an inner isolating layer of Eudragit® L30D with an outer layer comprising Eudragit® L30D and guar gum (Example 2).

WO96/36321A discloses an oral dosage form comprising a core containing bisacodyl, and an enteric polymer coating for the core, the coating comprising at least one inner coating layer and an outer coating layer. The or each of the inner coating layer(s) is an enteric polymer that begins to dissolve in an aqueous medium at a pH from about 5 to about 6.3, and the outer coating layer is an enteric polymer that begins to dissolve in an aqueous medium at a pH from about 6.8 to about 7.2. The enteric polymer coating materials for the inner layer(s) are selected from the group consisting of cellulose acetate phthalate; cellulose acetate trimellitate; hydroxypropyl methylcellulose phthalate; hydroxypropyl methylcellulose acetate succinate; polyvinyl acetate phthalate; poly(methacrylic acid, methyl methacrylate) 1:1; poly (methacrylic acid, ethyl acrylate) 1:1; and compatible mixtures thereof.

WO2013/164315A discloses a colonic drug delivery formulation comprising a core comprising a drug and a coating comprising an inner layer and an outer layer. A mixture of a pH dependent film-forming polymeric material and a polysaccharide such as starch is used as the outer layer and the inner layer is soluble in intestinal fluid or gastrointestinal fluid. The reference exemplifies inter alia formulations in which the outer layer is applied from "semi-organic" coating preparation. The "semi-organic" coating preparation is prepared from an aqueous dispersion of the polysaccharide and an organic (typically, ethanolic) solution of the pH dependent film-forming polymeric material.

The preparation of drug formulations requires the use of various excipients, such as fillers, disintegrants, plasticisers and flow regulators. A particularly important group of excipients used in the preparation of coating formulations are anti-tack (or anti-adherent) agents. Anti-tack agents are typically added to coating formulations to avoid sticking tendencies and the agglomeration of a powder or granulate during processing and storage. This helps to prevent adhesion of a tablet or a capsule to the surface to the walls and punches of the processing device. The most commonly used anti-tack agents are inorganic materials such as talc and colloidal silica. By way of example, WO2013/164315A describes the use of talc in combination with an aqueous coating preparation. WO2013/164315A also describes the use of the organic anti-tack agent, glyceryl monostearate (GMS) in coating formulations prepared using a "semi-organic" coating preparation as described above.

SUMMARY OF THE INVENTION

It would be desirable to provide an improved method for producing a delayed release drug formulation for delivering a drug to the colon.

In accordance with a first aspect of the present invention, there is provided a method of producing a delayed release drug formulation for oral administration to deliver a drug to the colon, said method comprising: forming a core comprising a drug; combining a first aqueous preparation of an enzymatically degradable polymer which is degradable by colonic bacterial enzymes (first polymeric material); a second aqueous preparation of a film-forming enteric polymer having a pH threshold of about pH 6 or above (second polymeric material); and an organic anti-tack agent, to form an outer layer coating preparation; and coating the core with the outer layer coating preparation to form an outer layer coated core.

DETAILED DESCRIPTION OF THE INVENTION

The Inventors have discovered that the use of an organic anti-tack agent applied from an aqueous outer layer preparation results in coatings which are more digestible in vitro by α-amylase and produces delayed release drug formulations which show improved gastric resistance and faster drug release profiles in Krebs buffer (pH 7.4).

The first aqueous preparation, the second aqueous preparation, and the organic anti-tack can be combined in any order. Preferably, the second aqueous preparation is added dropwise to the first aqueous preparation, followed by the organic anti-tack agent. The outer layer coating preparation is preferably a substantially homogenous dispersion or suspension.

In embodiments where the enzymatically degradable polymer is starch, it is preferred that the first aqueous preparation is prepared by dispersing the starch in at least one alcohol, preferably a $C_1$ to $C_6$ alcohol, e.g. methanol; ethanol; propan-1-ol; propan-2-ol; butan-1-ol; butan-2-ol; and mixtures thereof. It is particularly preferred to use butan-1-ol alone. Water then is usually added subsequently with good agitation. The resulting dispersion is usually heated to reflux (i.e. "cooked") and then cooled with stirring overnight to form the first aqueous preparation. The purpose of the alcohol(s) is to solvate the starch ready to form the aqueous dispersion. Alternatively, the polysaccharide can be dispersed directly in water.

In addition, where starch is used as the polysaccharide, the alcohol assists with stabilizing leached amylose during the cooking process. Specifically, it is believed that amylose forms V-complexes with butan-1-ol, which decrease the rate of crystallization upon cooling. The re-association of amylose into double helices is known as retrogradation and is thought to decrease the digestibility of the starch.

It is preferred that the second aqueous preparation is formed by suspending the enteric polymer in water under stirring to form a suspension, and partially neutralising the suspension with a base.

Preferably, the base is added to the suspension in an amount sufficient to neutralise from about 10% to about 30%, preferably from about 15% to 20%, of the carboxylic acid groups in the enteric polymer. In principle, any pharmaceutically acceptable base may be used. Preferred bases include potassium hydroxide and aqueous ammonia. A particularly preferred base is aqueous ammonia. Preferably, the aqueous ammonia has a concentration of from about 0.5 N to about 2 N, e.g. from about 0.5 N to 1.5 N, preferably about 1 N.

In preferred embodiments, the organic anti-tack agent is in the form of an aqueous dispersion. Preferably the aqueous dispersion comprises a surfactant. The surfactant is added to facilitate dispersion of the organic anti tack agent. In principle, any pharmacologically acceptable surfactant may be used. The surfactant is typically non-ionic and/or hydrophilic. A particularly preferred surfactant is polysorbate 80 (Tween® 80).

In principle, any pharmacologically acceptable organic anti-tack agent may be used. Preferred organic anti-tack agents include glyceryl monostearate (GMS) and stearic acid. The organic anti-tack agent is usually present in the outer layer coating preparation in an amount of from about 2 wt % and 20 wt %, e.g. from about 5 wt % to about 15 wt %, preferably about 7 wt % to about 12.5 wt %, most preferably about 10 wt %, based on the dry weight of the enteric polymer.

In preferred embodiments, the outer layer coating preparation comprises no more than 5% v/v organic solvent, preferably no more than 4% v/v, more preferably no more than 3% v/v, more preferably no more than 2% v/v, most preferably no more than 1% v/v.

In some embodiments, the core is pre-coated with either an isolation layer comprising a film-forming non-ionic polymer that is soluble in gastrointestinal fluid; or an inner layer comprising a polymeric material which is soluble in intestinal or gastrointestinal fluid (third polymeric material); or both the isolation layer and the inner layer. The third polymeric material is selected from the group consisting of a polycarboxylic acid polymer that is at least partially neutralised, and a non-ionic polymer, provided that, where the third polymeric material is a non-ionic polymer, the inner layer comprises at least one additive selected from a buffer agent and a base.

Enzymatically Degradable Polymer (First Polymeric Material)

The enzymatically degradable polymer is degraded or digested by one or more bacterial enzymes found in the colon of a subject (colonic bacterial enzymes). Such enzymes are produced by colonic bacteria and include amylases such as alpha-amylases, beta-amylases and iso-amlayses; amylopullunase, glucoamylase, alpha-glucosidase, maltogenic-amylase, glycosyltransferases and amylo-maltase.

The person skilled in the art is capable of determining whether a material is susceptible to attack by colonic bacterial enzymes using techniques comprising part of the common general knowledge. For example, a pre-determined amount of a given material could be exposed to an assay containing an enzyme from a bacterium found in the colon and the change in weight of the material over time may be measured. Alternatively, the amount of a degradation product produced as a result of the action of the colonic bacterial enzymes could be measured.

The enzymatically degradable polymer is preferably a polysaccharide. Suitable polysaccharides are selected from the group consisting of starch; amylose; amylopectin; chitosan; chondroitin sulfate; cyclodextrin; dextran; pullulan; carrageenan; sclerglucan; chitin; curdulan, levan and hemicellulose such as xylan, glucuronoxylan, arabinoxylan, glucomannam, xyloglucan. The polysaccharide is preferably starch. Starches are usually extracted from natural sources such as cereals; pulses; and tubers. Suitable starches for use in the present invention are typically food grade starches and include rice starch; wheat starch; corn (or maize) starch; pea starch; potato starch; sweet potato starch; tapioca starch; sorghum starch; sago starch; and arrow root starch. The use of maize starch is exemplified below.

Starch is typically a mixture of two different polysaccharides, namely amylose and amylopectin. Different starches may have different proportions of these two polysaccharides. Most natural (unmodified) maize starches have from about 20 wt % to about 30 wt % amylose with the remainder being at least substantially made up of amylopectin.

Suitable starches include "high amylose" and "low amylose" starches. High amylose starches are particularly preferred.

"High amylose" starches, are starches having at least 50 wt % amylose. Particularly suitable starches have from about 50 wt % to about 75 wt % amylose, preferably from about 50 wt % to about 70 wt %, more preferably from about 50 wt % to about 65 wt %, most preferably from about 50 wt % to about 60 wt %, e.g. about 55 wt %.

Low amylose" starches are starches having less than 50 wt % amylose and at least 50 wt % amylopectin, e.g. up to 75 wt % amylopectin and even as much as up to 99 wt % amylopectin.

Starches suitable for use in the present invention typically have at least 0.1 wt %, e.g. at least 10 wt % or 15 wt %, preferably at least 35 wt %, amylose. Such starches have no more than 99.9 wt %, e.g. no more than 90 wt % or 85 wt %, preferably no more than 65 wt %, amylopectin. Such starches may have up to about 99 wt % amylose and no less than 1 wt % amylopectin.

Starches suitable for use in the present invention may have up to 100% amylopectin, more typically from about 0.1 wt % to about 99.9 wt % amylopectin. The starch may be, for instance, unmodified waxy corn starch. This typically comprises about 100% amylopectin.

Preferred starches have no more than 50 wt % amylopectin. Particularly suitable starches have from about 25 wt % to about 35 wt % amylopectin, e.g. about 30 wt % amylopectin.

The person skilled in the art is capable of determining the relative proportions of amylose and amylopectin in any given starch. For example, near-infrared (NIR) spectroscopy could be used to determine the amylose and amylopectin content of a starch using calibration curves obtained by NIR using laboratory-produced mixtures of known amounts of these two components. Further, starch could be hydrolysed to glucose using amyloglucosidase. A series of phosphorylation and oxidation reactions catalysed by enzymes result in the formation of reduced nicotinamide adenine dinucleotide phosphate (NADPH). The quantity of NADPH formed is stoichiometric with the original glucose content. Suitable test kits for this procedure are available (e.g., R-Biopharm GmbH, Germany). Another method that could be used involves subjecting the coating to digestion by bacterial enzymes, e.g. α-amylase, to produce short chain fatty acids (SCFA) which can be quantified by gas-liquid chromatography using a capillary column.

Preferred starches are "off-the-shelf" starches, i.e. starches which require no processing prior to use in the context of the present invention. Examples of particularly suitable "high amylose" starches include Eurylon®6 (or VI) and Amylo N-400 (Roquette, Lestrem, France) or Amylogel 03003 (Cargill, Minneapolis, USA) all of which are examples of a maize starch having about 50-70 wt % amylose.

Film-Forming Enteric Polymer (Second Polymeric Material)

The film-forming enteric polymer is pH sensitive and has a pH threshold at about pH 6 or above. The "pH threshold" is the pH below which it is insoluble and at or above which it is soluble. The pH of the surrounding medium therefore triggers dissolution of the polymeric material. Thus, none (or essentially none) of the enteric polymer dissolves below the pH threshold. Once the pH of the surrounding medium reaches (or exceeds) the pH threshold, the second material becomes soluble.

By "insoluble" we mean that 1 g of the second material requires more than 10,000 ml of solvent (surrounding medium) to dissolve at a given pH.

By "soluble", we mean that 1 g of the second material requires less than 10,000 ml, preferably less than 5,000 ml, more preferably less than 1000 ml, even more preferably less than 100 ml or 10 ml of solvent to dissolve at a given pH.

"Surrounding medium" preferably means the medium in the gastrointestinal tract, such as the gastric juice or intestinal juice. Alternatively, the surrounding medium may be the in vitro equivalent of the medium in the gastrointestinal tract.

The normal pH of gastric juice is usually in the range of 1 to 3. The enteric polymer is insoluble below pH 6 and soluble at about pH 6 or above and, thus, is usually insoluble in gastric juice.

The pH of intestinal juice gradually increases from about 6 in the duodenum to about 7 to 8 in the distal small intestine. The enteric polymer is preferably insoluble below pH 6.5 (and soluble at about pH 6.5 or above) and, more preferably, is insoluble below pH 7 (and soluble at about pH 7 or above).

The pH threshold at which a material becomes soluble may be determined by a simple titration technique which would be part of the common general knowledge to the person skilled in the art.

Examples of suitable film-forming enteric polymers include an acrylate polymer, a cellulose polymer or a polyvinyl-based polymer. Examples of suitable cellulose polymers having a pH threshold of pH 6 or above include cellulose acetate phthalate (CAP) and hydropropylmethyl-cellulose acetate succinate.

The film-forming enteric polymer is preferably a co-polymer of a (meth)acrylic acid and a (meth)acrylic acid $C_{1-4}$ alkyl ester, for instance, a copolymer of methacrylic acid and methacrylic acid methyl ester. Such a polymer is known as a poly(methacrylic acid/methyl methacrylate) co-polymer. Suitable examples of such co-polymers are usually anionic and not sustained release polymethacrylates. The ratio of carboxylic acid groups to methyl ester groups (the "acid:ester ratio") in these co-polymers determines the pH at which the co-polymer is soluble. The acid:ester ratio may be from about 2:1 to about 1:3, e.g. about 1:1 or, preferably, about 1:2. The molecular weight (MW) of preferred anionic co-polymers is usually from about 120,000 to 150,000, preferably about 135,000.

Preferred anionic poly(methacrylic acid/methyl methacrylate) co-polymers include Eudragit® L (acid:ester ratio about 1:1; MW about 135,000; pH threshold of about 6); Eudragit® S 100 (acid:ester ratio about 1:2; MW about 135,000; pH threshold of about 7); and Eudragit® FS (a poly(methyl acrylate/methyl methacrylate/methacrylic acid); acid:ester ratio of about 1:10; MW about 220,000; pH threshold of about 7).

The film-forming enteric polymer may be a copolymer of methacrylic acid and ethyl acrylate. Eudragit® L100-55 poly(methacrylic acid/ethyl acrylate); acid:ester ratio of about 1:1; MW about 250,000; pH threshold of about 6. The Eudragit® co-polymers are manufactured and/or distributed by Evonik, Darmstadt, Germany.

Mixtures of film-forming enteric polymers may be used as appropriate. An example of a suitable mixture would include a mixture, e.g. a 1:1 mixture, of Eudragit® L and Eudragit® S 100. However, the use of a particular film forming polymer material, e.g. a poly(methacrylic acid/methyl methacrylate) co-polymer, alone is preferred.

The use of Eudragit® S 100 alone as the film-forming enteric polymer is particularly preferred.

Preferably, the exemplary polymers are used as the film-forming enteric polymer in the outer layer in at least partially neutralized form, i.e. that at least a portion, e.g. at least 10%, preferably between 15% and 20% (on a molar basis) of the carboxylic acid groups in are the form of carboxylate anions.

Outer Layer

The proportion of the enzymatically degradable polymer to the film-forming enteric polymer is typically at least 1:99, e.g. at least 10:90 and preferably at least 25:75. The proportion is typically no more than 99:1, e.g. no more than 75:25 and preferably no more than 60:40. In some embodiments, the proportion may be no more than 35:65. In some preferred embodiments, the proportion is from 10:90 to 75:25, e.g. from 10:90 to 60:40 and preferably from 25:75 to 60:40. In some particularly preferred embodiments, the proportion is from 15:85 to 35:65, e.g. from 25:75 to 35:65 and preferably about 30:70. In other particularly preferred embodiments, the proportion is from 40:60 to about 60:40, e.g. about 50:50.

The thickness of the outer layer coating of the core is typically from about 10 μm to about 300 μm. The thickness of a specific coating will, however, depend on the composition of the coating and on the size of the core. For example, coating thickness is directly proportional to the amount of polysaccharide in the coating.

Thus, in embodiments where the outer layer coating comprises high amylose starch and Eudragit® S at a ratio of about 30:70, the coating thickness may be from about 70 μm to about 300 μm, and preferably from about 150 μm to about 250 μm. The thickness (in μm) for a given coating composition is dependent on core size.

The amount of enteric polymer in the outer layer is not related to the size of the core. The outer coating typically has a coating amount of enteric polymer of from about 2 mg/cm$^2$ to about 10 mg/cm$^2$, e.g. from about 2 mg/cm$^2$ to about 8 mg/cm$^2$, or from about 3 mg/cm$^2$ to about 8 mg/cm$^2$, or from about 4 mg/cm$^2$ to about 8 mg/cm$^2$, or from about 5 mg/cm$^2$ to about 8 mg/cm$^2$, or from about 6 mg/cm$^2$ to about 8 mg/cm$^2$, or from about 7 mg/cm$^2$ to about 8 mg/cm$^2$, e.g. about 7.5 mg/cm$^2$. A typical core has a diameter of from about $5 \times 10^{-4}$ m to about 25 mm.

In addition to the organic anti-tack agent, the outer layer coating preparation may optionally comprise one or more conventional excipients for polymer films, such as plasticisers for film formation (e.g. triethyl citrate), surfactants (e.g. polysorbate 80), and pigments (e.g. iron oxide red or iron oxide yellow).

Third Polymeric Material

The core may be coated directly with said outer layer coating preparation, or the core may optionally be pre-coated with an inner layer coating preparation to form an inner layer coated core. The inner layer comprises a film-forming polymer (third polymeric material) which is soluble in intestinal fluid or gastrointestinal fluid (both gastric and intestinal fluid).

The third polymeric material is selected from the group consisting of a polycarboxylic acid polymer that is at least partially neutralised, and a non-ionic polymer, provided that, where the polymeric material is a non-ionic polymer, the inner layer comprises at least one additive selected from a buffer agent and a base.

By "gastric fluid", the inventors mean the aqueous fluid in the stomach of a mammal, particularly a human. The fluid contains up to about 0.1 N hydrochloric acid and substantial quantities of potassium chloride and sodium chloride, and plays a key role in digestion by activating digestive enzymes and denaturing ingested protein. Gastric acid is produced by cells lining the stomach and other cells produce bicarbonate which acts as a buffer to prevent the gastric fluid from becoming too acidic.

By "intestinal fluid", the Inventors mean the fluid in the lumen of the intestine of a mammal, particularly a human. Intestinal fluid is a pale yellow aqueous fluid secreted from glands lining the walls of the intestine. Intestinal fluid includes fluid found in the small intestine, i.e. fluid found in the duodenum (or "duodenal fluid"), fluid found in the jejunum (or "jejunal fluid") and fluid found in the ileum (or "ileal fluid"), and fluid found in the large intestine, e.g. "colonic fluid".

The skilled person can readily determine whether a polymer is soluble in gastric fluid and/or intestinal fluid. If a polymer is soluble in water (or aqueous solution), e.g. a buffer solution) at a pH from 1 to 3, then that polymer would typically be soluble in gastric fluid. Similarly if a polymer is soluble in water (or aqueous solution, e.g. a buffer solution) at a pH from 5 to 8, then that polymer would typically be soluble in intestinal fluid. Alternatively, the compositions of gastric fluid and intestinal fluid are known and may be replicated in vitro. If a polymer is soluble in artificial gastric fluid or intestinal fluid in vitro, then it would typically be soluble in gastric fluid or intestinal fluid respectively in vivo.

Any pharmacologically acceptable water-soluble polycarboxylic acid polymers and non-ionic polymers are, in principle, suitable for use as the third polymeric material. The solubility of the water soluble polymers may be dependent on pH, i.e. the polymeric material may be a pH sensitive polymer having a pH threshold.

The polymeric material may be soluble in at least one fluid selected from gastric fluid, duodenal fluid, jejunal fluid and ileal fluid. However, in preferred embodiments, the solubility of the third polymeric material in water is not dependent on pH; at least not within the range of pH found in the intestine. In preferred embodiments, the third polymeric material is soluble in fluid at any point in the stomach and intestine, i.e. in gastrointestinal fluid.

Polycarboxylic acid polymers ("anionic" polymers) are polymers or co-polymers that contain a plurality of carboxylic acid functional groups that are ionisable in aqueous media such as intestinal fluid, to form carboxylate anions.

In embodiments in which the third polymeric material is a polycarboxylic acid polymer, the third polymeric material is at least partially neutralised, i.e. that at least a portion, e.g. at least 10%, preferably at least 25%, more preferably at least 50%, and most preferably at least 90%, of the carboxylic acid groups are in the form of carboxylate anions. In particularly preferred embodiments, all of the carboxylic acid groups in the third polymeric material are in the form of carboxylate anions. Such polymers are referred to herein as "fully neutralised".

In preferred embodiments, the second and third polymeric materials are based on the same polycarboxylic acid polymer with the third polymeric material having a higher degree of neutralisation than the second polymeric material. For example, for a particular polycarboxylic acid polymer, the second polymeric material may be in non-neutralised form with the third polymeric material in partially or fully neutralised form. Alternatively, the second polymeric material may be in partially neutralised form, with the third polymeric material also in partially neutralised form (although partially neutralised to a greater extent), or in fully neutralised form.

Examples of suitable polycarboxylic acid polymers include cellulose acetate phthalate (CAP), polyvinyl acetate phthalate (PVAP), hydroxypropyl methylcellulose phthalate (HPMCP), hydroxypropyl methylcellulose acetate succinate (HPMC-AS), cellulose acetate trimellitate (CAT), xanthan gum, alginates and shellac. However, the polycarboxylic acid polymer is preferably selected from co-polymers of a (meth)acrylic acid and a (meth)acrylic acid alkyl, e.g. $C_{1-4}$ alkyl, ester and a copolymer of methacrylic acid and methacrylic acid methyl ester is particularly suitable. Such a polymer is known as a poly(methacrylic acid/methyl methacrylate) co-polymer or a "polymethacrylate". The ratio of carboxylic acid groups to methyl ester groups (the "acid:ester ratio") in these co-polymers determines the pH at which the co-polymer is soluble. The acid:ester ratio may be from about 2:1 to about 1:3, e.g. about 1:1 or, preferably, about 1:2. The molecular weight (MW) of preferred anionic co-polymers is usually from about 120,000 to 150,000, preferably about 125,000 or about 135,000.

Preferred co-polymers for the third polymeric material are discussed in detail in the section above relating to the second polymeric material, and include Eudragit® L; Eudragit® S; Eudragit® FS 30 D; Eudragit® L30D-55; and Eudragit® L100-55.

Preferably, the exemplary polymers are used as the third polymeric material is in at least partially, more preferably fully, neutralised form.

Partially neutralised polymers suitable for use as the third polymeric material, and their methods of production, are known in the art, for example from US2008/0200482A and WO2008/135090A. These polymers may be fully neutralised by the addition of further base to the coating solutions.

In preferred embodiments, the third polymeric material is an at least partially, preferably fully, neutralised co-polymer of (meth)acrylic acid and a (meth)acrylic acid $C_{1-4}$ alkyl ester. In particularly preferred embodiments, the third polymeric material is a fully neutralised co-polymer of (meth)acrylic acid and (meth)acrylic acid methyl ester, particularly Eudragit® S.

The Inventors have observed that fully neutralised Eudragit® S is capable of forming a film and is readily and completely soluble in water independently of at least the range of pH found in the intestine, e.g. about pH 5 to about pH 8. Fully neutralised Eudragit® S is particularly preferred for use as the third polymeric material in the present invention.

Other polymers suitable for use as the third polymeric material include pharmacologically acceptable non-ionic polymers, i.e. pharmacologically acceptable polymers which do not ionise in aqueous media. In these embodiments, the inner layer additionally comprises at least one additive selected from a buffer agent and a base. In particular, the inner layer of these embodiments preferably comprises a base and, optionally, a buffer agent. In preferred embodiments, the inner layer comprises both a buffer agent and a base. Suitable examples of buffer agents and bases are discussed below.

It is preferred that the non-ionic polymer of the inner layer is a non-ionic cellulose-based polymer. Examples of suitable non-ionic cellulose-based polymers include methylcellulose (MC), hydroxypropyl cellulose (HPC), hydroxypropyl methylcellulose (HPMC). A particularly preferred non-ionic cellulose-based polymer is HPMC. Non-cellulose based polymers such as poly(ethyleneoxide)-graft-polyvinylalcohol, polyvinylpyrrolidinone (PVP), polyethylene glycol (PEG), PVP-grafted PEG and polyvinylalcohol (PVA) are also preferred.

Mixtures of film-forming polymer materials may be used as appropriate. The polymer components in such mixtures may be polycarboxylic acid polymers, non-ionic polymers, or a mixture of polycarboxylic acid polymers and non-ionic polymers. An example of a suitable mixture would include a mixture, e.g. a 1:1 mixture, of Eudragit® L and Eudragit® S, and a mixture, e.g. a 1:1 mixture, of Eudragit® S and HPMC. However, the use of a particular film-forming polymeric material alone, e.g. a poly(methacrylic acid/methyl methacrylate) co-polymer and Eudragit® S in particular, is preferred.

Base

In preferred embodiments, the inner layer comprises at least one base. The purpose of the base is to provide an alkaline environment on the underside of the outer layer once intestinal fluid begins to penetrate the outer layer. Without being bound by any particular theory, the Inventors believe that the alkaline environment facilitates dissolution and thereby also disintegration of the outer layer since the pH of the alkaline environment is above the pH threshold of the second polymeric material, thereby accelerating release of the drug from the formulation once the outer coating is dissolved and/or disintegrates.

In principle, any pharmacologically acceptable base may be used. The base is typically a non-polymeric compound. Suitable bases include inorganic bases such as sodium hydroxide, potassium hydroxide and ammonium hydroxide, and organic bases such as triethanolamine, sodium bicarbonate, potassium carbonate, trisodium phosphate, trisodium citrate or physiologically tolerated amines such as triethylamine.

The base is preferably selected from the group consisting of hydroxide bases, alkali metal bicarbonates, alkali metal carbonates, alkali metal phosphates, alkali metal citrates, or physiologically tolerated amines. More preferably, the base is a hydroxide base, and particularly preferred is sodium hydroxide.

In embodiments in which the third polymeric material is a fully neutralised polycarboxylic acid polymer, the base entrapped within the inner layer is usually the base that was used to neutralise the polymer and to adjust the pH of the inner coating preparation to a pH from about pH 7.5 to about pH 10 (see below).

In embodiments in which the third polymeric material is a non-ionic polymer, the inner layer usually comprises either a base, or more typically a combination of a base and a buffer agent.

The amount of base present in the inner layer would depend at least in part on the final pH of the inner coating preparation prior to coating a given batch of cores; the number of cores to be coated in the batch; the amount of the inner layer coating preparation used in the coating process of the batch.

Buffer Agent

The inner layer preferably comprises at least one buffer agent. The purpose of the buffer agent is to provide or increase buffer capacity on the underside of the outer layer once intestinal fluid begins to penetrate the outer layer. Without wishing to be bound by any particular theory, the Inventors believe that the buffer agent increases the buffer capacity in the dissolving inner layer and assists the ionisation and dissolution of the polymer in the outer layer. For a given pH, the higher the buffer capacity, the faster the rate of polymer dissolution.

In embodiments where there is a base in the inner layer, the buffer agent helps maintains the alkaline environment under the outer layer once intestinal fluid penetrates the outer layer.

The buffer agent can be any suitable buffer agent known by the skilled person. The buffer agent may be an organic acid such as a pharmacologically acceptable non-polymeric carboxylic acid, e.g. a carboxylic acid having from 1 to 16, preferably 1 to 3, carbon atoms. Suitable carboxylic acids are disclosed in WO2008/135090A. Citric acid is an example of such a carboxylic acid. The carboxylic acids may be used in carboxylate salt form, and mixtures of carboxylic acids, carboxylate salts or both may also be used.

The buffer agent may also be an inorganic salt such as an alkali metal salt, an alkali earth metal salt, an ammonium salt, and a soluble metal salt. As metals for the soluble metal salts, manganese, iron, copper, zinc and molybdenum can be mentioned. Further preferred, the inorganic salt is selected from chloride, fluoride, bromide, iodide, phosphate, nitrate, nitrite, sulphate and borate. Phosphates such as potassium dihydrogen phosphate are preferred over other inorganic buffer salts and organic acid buffers due to their greater buffer capacity at the pH of the coating solution, for example pH 8.

The buffer(s) is usually present in the inner layer in an amount from about 0.1 wt % to about 60 wt %, e.g. from about 0.1 wt % to about 50 wt %, preferably from about 0.1 wt % to about 40, more preferably from about 0.1 to about 20 wt %, more preferably from about 0.1 wt % to about 4 wt %, more preferably from about 0.1 wt % to about 3 wt %, and most preferably about 1 wt %, based on the dry weight of the third polymeric material.

Inner Layer

The thickness of the inner layer coating of the core is typically from about 10 µm to about 150 µm. As with the outer coating layer, the thickness of a specific coating will depend on the composition of the coating and on the size of the core.

As with the outer layer, the amount of polymer in the inner layer is not related to the size of the core. The inner layer typically has a coating amount of the third polymeric material of from about 2 mg/cm$^2$ to about 5 mg/cm$^2$, e.g. about 3 mg/cm$^2$, based on the dry weight of the third polymeric material.

In addition to the buffer agent and/or the base, the inner layer may comprise conventional excipients for polymer films, including those excipients selected from plasticisers (e.g. triethyl citrate), anti-tack agents (e.g. GMS), and surfactants (e.g. polysorbate 80).

Additional Layers

The core may be coated directly using either said inner layer coating preparation or said outer layer coating preparation. Alternatively, the core may be pre-coated using an isolation layer coating preparation to form an isolation layer coated core which is then coated using said inner layer coating preparation and/or said outer layer coating preparation.

An isolation layer may be desirable when the composition of the core is incompatible with the delayed release coating. For example, the present invention embraces embodiments in which the inner layer provides an alkaline environment which is thought to assist in the dissolution and degradation of the outer layer. However, if the core contains a drug having acidic groups, then the inner layer may be incompatible with the core. An example of a drug having an acidic group would be 5-ASA. In such cases, it would typically be appropriate to include an isolation layer.

Any suitable isolation layer known to the skilled person can be used. In one preferred embodiment, the isolation layer comprises a film-forming non-ionic polymer. Suitable non-ionic polymers include methylcellulose (MC); hydroxypropyl cellulose (HPC); hydroxypropyl methylcellulose (HPMC); poly(ethyleneoxide)-graft-polyvinylalcohol; polyvinylpyrollidone (PVP); polyethylene glycol (PEG); and polyvinylalcohol (PVA). Non-ionic cellulose based polymers (such as HPMC) are preferred, as is PVA. Mixtures of non-ionic polymers can also be used. A particularly preferred mixture is HPMC and PEG. The isolation layer can additionally comprise a plasticiser. Suitable plasticisers include but are not limited to polyethylene glycol, triethyl citrate, triacetin and acetyltriethyl citrate.

It is also possible to have an intermediate layer between the outer and inner layers, provided that the intermediate layer does not affect adversely the release characteristics of the formulation. However, the outer layer is usually provided in contact with the inner layer, that is to say the outer layer is usually applied directly on to the inner layer, i.e. there is usually no intermediate layer separating the inner and outer layers.

The Core

The "core" is the solid body on which the coating is applied. The core may be any suitable dosage form, for example, a tablet, a pellet, a granule, a microparticle, a hard or soft capsule, or a microcapsule. In preferred embodiments, the core is a tablet or a capsule.

The core comprises the drug(s). The drug(s) may be contained within the body of the core, for example within the matrix of a tablet or a pellet, or within the contents encapsulated within a capsule. Alternatively, the drug may be in a coating applied to the core, for example where the core is a bead of edible material such as sugar, e.g. where the core is in the form of a nonpareil bead or dragée.

The core may consist of the drug(s) alone, or more usually may consist of the drug(s) and at least one pharmacologically acceptable excipient. In this connection, the core is typically a tablet or pellet and usually consists of a mixture of the drug(s) with one more excipients selected from a filler or diluent material, e.g. lactose or cellulose material such as microcrystalline cellulose; a binder, e.g. polyvinylpyrrolidone (PVP) or hydroxypropyl methylcellulose (HPMC); a disintegrant, e.g. croscarmellose sodium (e.g. Ac-Di-Sol™) and sodium starch glycolate (e.g. Explotab™); and/or a lubricant, e.g. magnesium stearate and talc. The core may be a compressed granulate comprising at least some of these materials.

The core may be uncoated or, the core may be pre-coated with an isolation layer and/or an inner layer onto which the outer layer coating is directly applied. The isolation layer and the inner layer are discussed in more detail above.

The minimum diameter of each core is typically at least about $10^{-4}$ m, usually at least about $5 \times 10^{-4}$ m and, preferably, at least about $10^{-3}$ m. The maximum diameter is usually no more than 30 mm, typically no more than 25 mm and, preferably, no more than 20 mm. In preferred embodiments, the core has a diameter from about 0.2 mm to about 25 mm, and preferably from about 0.2 mm to about 4 mm (e.g. for pellets or mini-tablets) or from about 5 mm to about 25 mm (e.g. for certain tablets or capsules). The term "diameter" refers to the largest linear dimension through the core.

Different Aspects

According to a second aspect of the present invention there is provided a delayed release drug formulation for oral administration to deliver a drug to the colon. The formulation comprises:

a core comprising a drug, and an outer coating layer for the core, the outer coating layer comprising a mixture of an enzymatically degradable polysaccharide which is degradable by colonic bacterial enzymes, a film-forming enteric polymer having a pH threshold at about pH 6 or above, and an organic anti-tack agent;

wherein the outer coating layer comprises no more than 5000 ppm residual free organic solvent;

and/or wherein the outer coating layer comprises at least 10% by weight of at least one plasticiser based on the total weight of the film-forming enteric polymer.

In embodiments according to the second aspect of the invention, the core may be coated directly with the outer coating layer. Alternatively, an optional isolation layer and/or inner layer may be located between core and the outer coating layer.

The optional inner layer is as defined above and comprises a polymeric material which is soluble in intestinal or gastrointestinal fluid. The optional isolation layer is as defined above, and comprises a film-forming non-ionic polymer that is soluble in gastrointestinal fluid.

The outer coating layer typically comprises no more than 5000 ppm residual free organic solvent, for example no more than about 4000 ppm, or no more than about 3000 ppm, or no more than about 2000 ppm, or no more than about 1000 ppm, or no more than about 750 ppm, or no more than about 500 ppm, or no more than about 250 ppm, or no more than about 100 ppm, or no more than about 75 ppm, or no more than about 50 ppm, or no more than about 25 ppm, or no more than about 10 ppm.

The outer coating layer typically comprises at least about 10% by weight of at least one plasticiser (e.g. TEC), for example, at least about 15%, or at least about 20%, or at least about 30%, or at least about 40%, or at least about 50%. The outer coating typically comprises no more than about 70% by weight of at least one plasticiser, e.g. about 60% by weight.

The formulation may comprise a plurality of coated cores in order to provide a single dose of the drug(s), particularly in embodiments in which the core is "small", e.g. having a diameter of less than 5 mm. Multiunit dosage forms comprising coated cores having a diameter of less than 3 mm may be preferred.

The present invention has application in a multi-phasic drug release formulation comprising at least two pluralities of coated cores, e.g. coated pellets, in the same dosage form, e.g. a capsule, in which the coated cores of one plurality are differentiated from the coated cores of the or each other plurality by the coating. The coatings may differ from one plurality to the next in terms of coating thickness or composition, e.g. the ratio and/or identity of components. Multiphasic drug release formulations would be particularly suitable for suffers of Crohn's disease affecting different regions along the intestine.

Release from formulations according to the present invention is typically delayed until at least the distal ileum and, preferably, the colon. Release from certain formulations may also be sustained. However, in preferred formulations, release is pulsatile.

The time between initial exposure to conditions suitable for drug release and the start of drug release is known as the "lag time". The lag time depends on a number of factors including coating thickness and composition and may vary from one patient to the next. Formulations according to the present invention usually display a lag time in colonic conditions of at least 10 minutes. In most embodiments, the lag time is from about 10 minutes to about 4 hours. Complete release of the drug may be achieved in no more than 5 hours, e.g. no more than 4 hours, after exposure to these conditions.

A formulation is usually defined as gastric resistant if there is less than 10 wt % drug release in acidic media after 2 hours. Formulations according to the present invention typically display far less than 10 wt % drug release in acidic media and may be considered to be gastric resistant. The formulations usually display less than 1 wt % drug release in acidic media and, typically, display substantially no drug release in acidic media. When starch is combined with an acrylate film-forming material to form the outer layer of the coating for the core, typically less than 5% drug release occurs over 6 hours in conditions simulating the stomach and small intestine.

The core comprises at least one drug. The formulation is usually used to administer a single drug as the sole therapeutically active component. However, more than one drug may be administered in a single formulation.

The formulation of the present invention is designed to administer a wide range of drugs. Suitable drugs include those drugs which are known for intestinal administration using known delayed release oral formulations. The present invention may be used to administer drugs having a local or a systemic effect.

The formulation of the present invention has particular application in the intestinal administration of a drug comprising at least one acidic group such as a carboxylic acid group. Such drugs may be acidic drugs or zwitterionic drugs. An example of such a drug is 5-aminosalicylic acid (5-ASA, otherwise known as mesalamine or mesalazine).

The identity of the drug(s) in the formulation obviously depends on the condition to be treated. In this connection, the formulation has particular application in the treatment of IBD (including Crohn's disease and ulcerative colitis); IBS; constipation; diarrhoea; infection; and carcinoma, particularly colon or colorectal cancer.

For the treatment or prevention of IBD, the formulation may comprise at least one drug selected from the group consisting of anti-inflammatory agents (e.g. 5-ASA, 4-ASA, sulphasalazine and balsalazide); non-steroidal anti-inflammatory agents (e.g. ibuprofen and diclofenac); steroids (e.g. prednisolone; budesonide or fluticasone); immunosuppressants (e.g. azathioprine; cyclosporin; and methotrexate); antibiotics; and biological agents including peptides, proteins and antibody fragments. Suitable examples of biological agents include alkaline phosphatase and anti-TNF antibodies such as infliximab, adalimumab, certulizumab pegol, golimumab and ustekinumab.

For the treatment or prevention of cancer, the formulation may comprise at least one antineoplastic agent. Suitable antineoplastic agents include fluorouracil; methotrexate; dactinomycin; bleomycin; etoposide; taxol; vincristine; doxorubicin; cisplatin; daunorubicin; VP-16; raltitrexed; oxaliplatin; and pharmacologically acceptable derivatives and salts thereof. For the prevention of colon cancer or colorectal cancer, primarily in patients suffering from colitis, the formulation may comprise the anti-inflammatory agents 5-ASA, sulindac, celecoxib and/or eflornithine (DFMO).

For the treatment or prevention of IBS, constipation, diarrhoea or infection, the formulation may comprise at least one active agent suitable for the treatment or prevention of these conditions.

Pharmacologically acceptable derivatives and/or salts of the drugs may also be used in the formulation. An example of a suitable salt of prednisolone is methyl prednisolone sodium succinate. A further example is fluticasone propionate.

The present invention has particular application in either the treatment of IBD (particularly, ulcerative colitis) or the prevention of colon cancer or colorectal cancer (primarily in colitis patients), both using 5-ASA. It also has application as a portal of entry of drugs into the systemic circulation via the colon. This is particularly advantageous for peptide and protein drugs which are unstable in the upper gastrointestinal tract. The present invention may also be utilised for the purpose of chronotherapy.

The formulation will typically comprise a therapeutically effective amount of the or each drug which may be from about 0.01 wt % to about 99 wt %, based on the total weight of the formulation. The actual dosage would be determined by the skilled person using his common general knowledge. However, by way of example, "low" dose formulations typically comprise no more than about 20 wt % of the drug, and preferably comprise from about 1 wt % to about 10 wt %, e.g. about 5 wt %, of the drug. "High" dose formulations typically comprise at least 40 wt % of the drug, and preferably from about 45 wt % to about 85 wt %, e.g. about 50 wt % or about 80 wt %.

The formulation of the present invention can comprise any size core. In some embodiments, the drug can be present in the core of the formulation in an amount of from about 50 mg to about 1650 mg, or from about 100 mg to about 1550 mg, or from about 150 mg to about 1500 mg, or from about 200 mg to about 1450 mg, or from about 250 mg to about 1400 mg, or from about 300 mg to about 1350 mg, or from about 350 mg to about 1300 mg, or from about 400 mg to about 1250 mg, or from about 450 mg to about 1200 mg, or from about 500 mg to about 1150 mg, or from about 550 mg to about 1100 mg, or from about 600 mg to about 1050 mg, or from about 650 mg to about 1000 mg, or from about 700 mg to about 950 mg, of from about 800 mg to about 1600 mg, or from about 850 mg to about 1600 mg, or from about 900 mg to about 1500 mg, or from about 950 mg to about 1400 mg or from about 1000 to about 1300 mg, or from about 1150 about 1200 mg. Preferably, the drug is present in the core amount selected from about 400 mg, about 800 mg, about 1200 mg, about 1500 mg, or about 1600 mg.

The formulations of the present invention may be prepared using the methods discussed above.

EXAMPLES

Preferred embodiments of the present invention will now be described with reference to the drawings, in which:—

Figure 1:
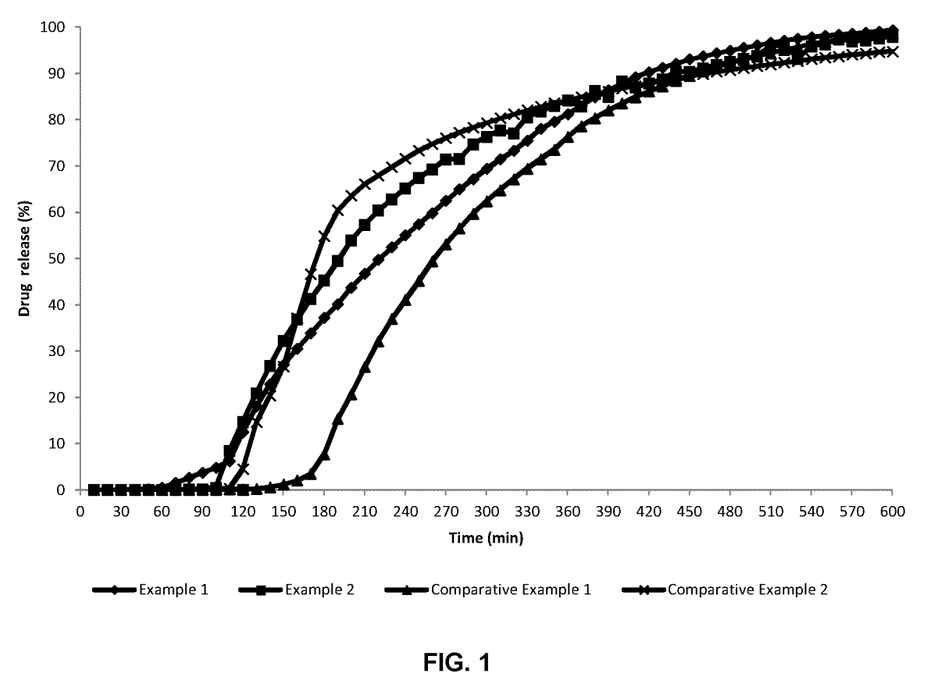
FIG. 1 shows a graph comparing drug release as a function of time from coated 5-ASA capsules according to Examples 1-2 and Comparative Examples 1-2.
Figure 2:
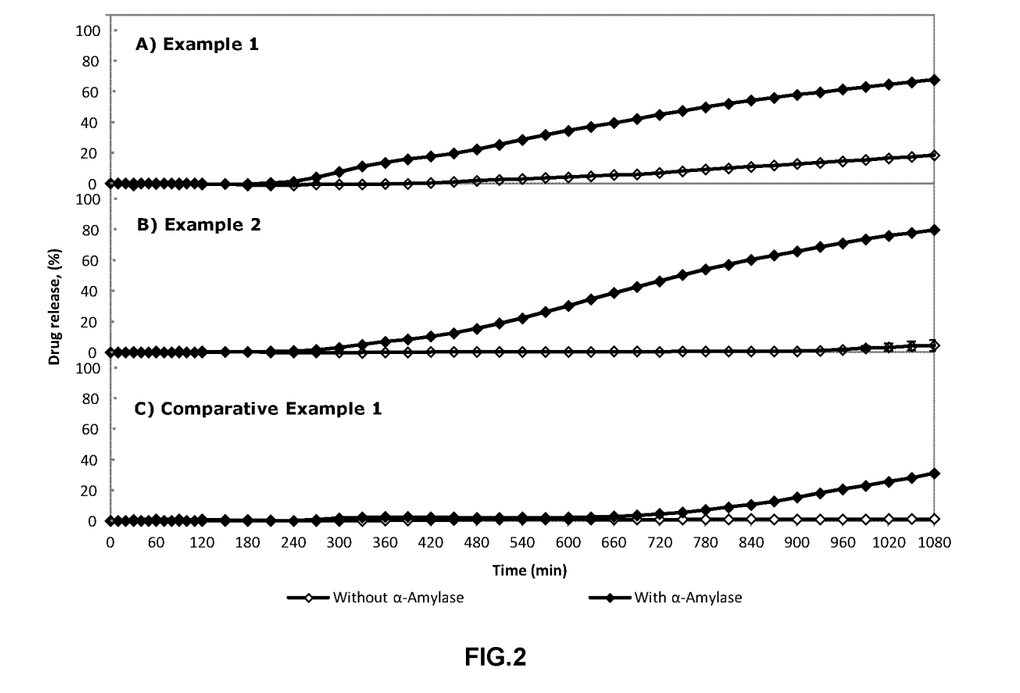
FIG. 2 shows a graph comparing drug release as a function of time from coated 5-ASA capsules according to Examples 1-2 and Comparative Example 1.

FIG. 1 is a graph comparing drug release as a function of time from coated 5-ASA capsules according to Examples 1, Example 2, Comparative Example 1 and Comparative Example 2, when exposed to 0.1M HCl for 2 hours (data not shown) and then Krebs's buffer (pH 7.4) for 10 hours;

FIG. 2 is a graph comparing drug release as a function of time from coated 5-ASA capsules according to Example 1, Example 2 and Comparative Example 1, when exposed to 0.1N HCl for 2 hours (data not shown) and then Sørensen's buffer (pH 6.8) for about 18 hours (a) with α-amylase and (b) without α-amylase.

Figure 3:
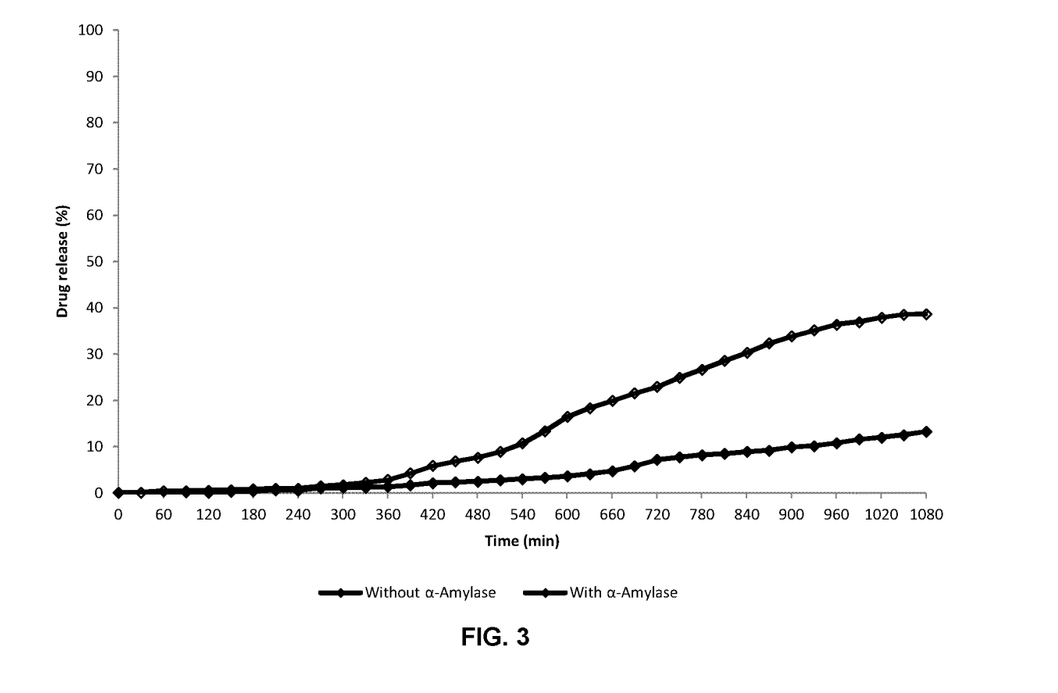
FIG. 3 shows a graph comparing drug release as a function of time from coated 5-ASA capsules according to Comparative Example 2.

FIG. 3 is a graph comparing drug release as a function of time from coated 5-ASA capsules according to Comparative Example 2, when exposed to 0.1N HCl for 2 hours (data not shown) and then Sørensen's buffer (pH 6.8) for about 18 hours (a) with α-amylase and (b) without α-amylase.

Figure 4:
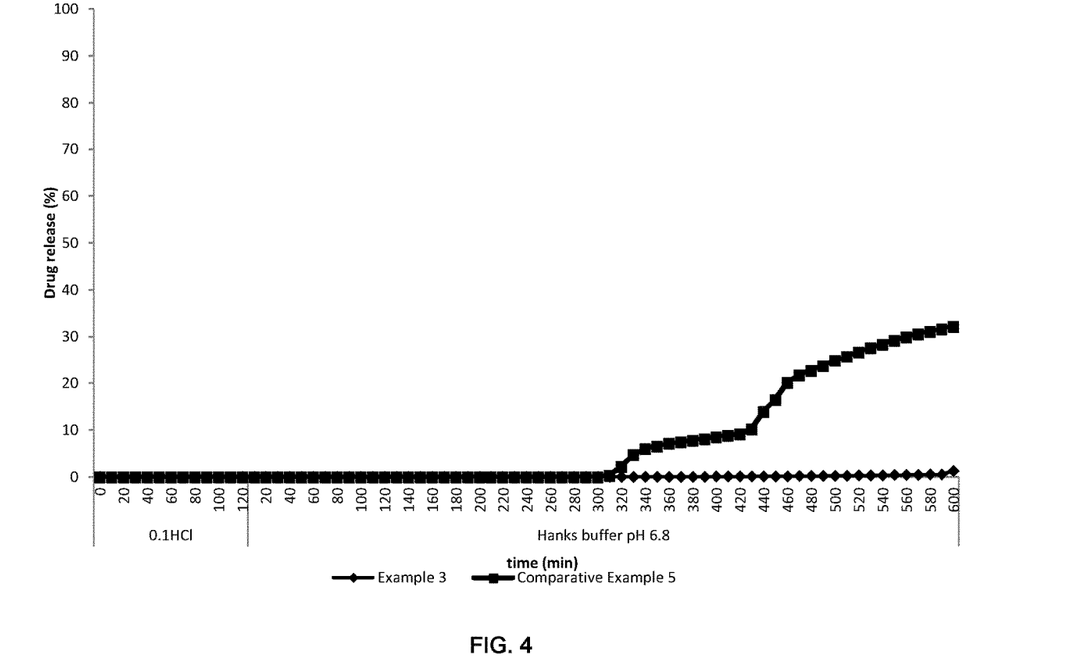
FIG. 4 shows a graph comparing drug release as a function of time from coated 1600 mg 5-ASA tablets according to Example 3 and Comparative Example 5.
Figure 5:
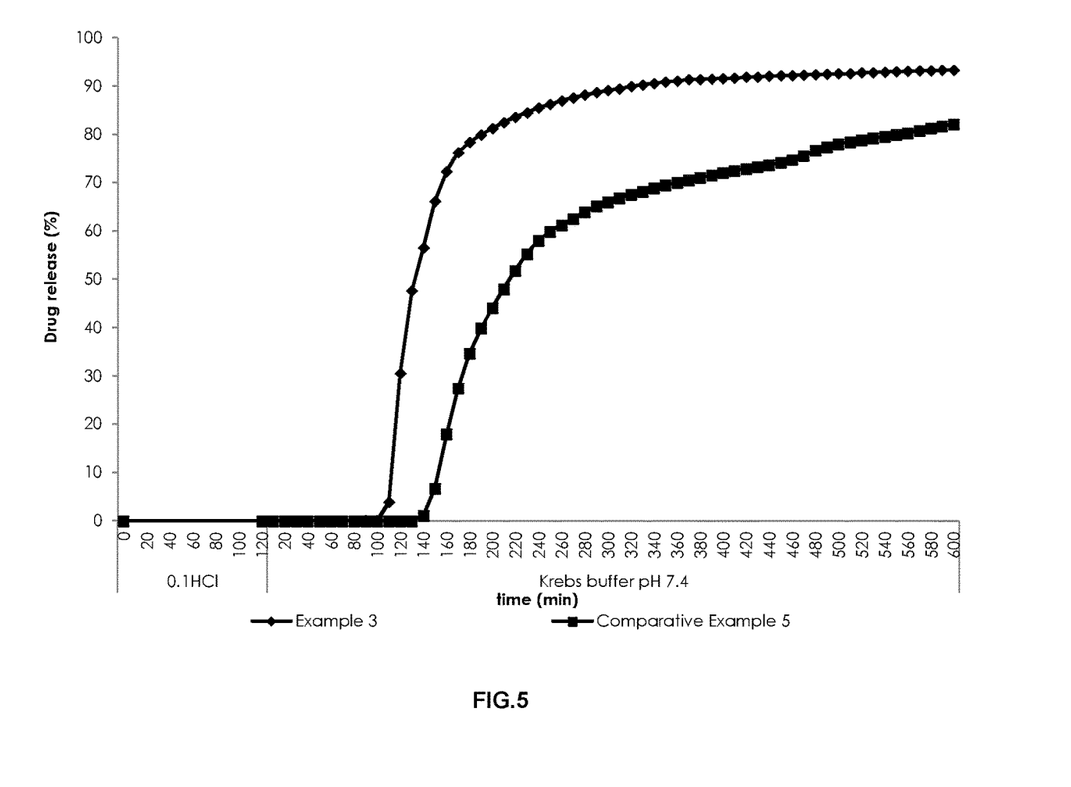
FIG. 5 shows a graph comparing drug release as a function of time from coated 1600 mg 5-ASA tablets according to Example 3 and Comparative Example 5.

FIG. 4 is a graph comparing drug release as a function of time from coated 1600 mg 5-ASA tablets according to Example 3 and Comparative Example 5, when exposed to 0.1M HCl for 2 hours and then Hank's buffer (pH 6.8) for 10 hours;

FIG. 5 is a graph comparing drug release as a function of time from coated 1600 mg 5-ASA tablets according to Example 3 and Comparative Example 5, when exposed to 0.1M HCl for 2 hours and then Krebs's buffer (pH 7.4) for 10 hours;

MATERIALS

Eudragit® S 100, was purchased from Evonik GmbH, Darmstadt, Germany. Maize starch (Eurylon 6) was purchased from Roquette, Lestrem, France. Polysorbate 80 (Tween 80), butan-1-ol, triethyl citrate (TEC), ethanol 95%, talc, potassium phosphate monobasic ($KH_2PO_4$), sodium diphosphate dibasic dihydrate ($Na_2HPO_4 \cdot 2H_2O$), and sodium hydroxide were all purchased from Sigma-Aldrich, Buchs, Switzerland. Syloid 244 FP was received from Grace, Discovery Sciences, Belgium and Aerosil 300 from Evonik GmbH, Darmstadt, Germany. HPMC (Pharmacoat 603) was purchased from Shin-Etsu and hydroxypropyl methylcellulose (HPMC, Methocel E3 or Methocel E5) was purchased from Colorcon. Glyceryl monostearate (GMS) was purchased from Cognis. (Polyethylene glycol (PEG) was purchased from Aldrich. Iron oxide red and iron oxide yellow (Sicovit) were purchased from BASF. HPMC capsules were purchased from Qualicaps. Gelatin was purchased from Gelita. Ammonia solution (25%) was purchased from VWR International LTD, Poole, UK.

Preparation of Gelatin Banded Capsule Cores

5-ASA granules were prepared by mixing 5-ASA with an aqueous solution of HPMC in a high shear granulator at 550 rpm. The granules were passed through a 6.34 mm sieve (Comil) before drying at 45° C. The dry granules were then sieved through a 1.6 mm conical mill.

Capsules of size 00 were filled with 550 mg to 630 mg of the dry 5-ASA granules and the capsules were banded with a 21.8% gelatin solution and dried at room temperature.

Preparation of Tablet Cores

Oblong shaped 1600 mg cores were prepared according to the following method. The amount of each component per tablet core is: 160 mg mesalazine, 32 mg hypromellose, 178 mg microcrystalline cellulose, 54 mg sodium starch glycolate, 2 mg colloidal silicon dioxide and 1 mg magnesium stearate.

Mesalazine (8 kg) and an aqueous solution containing HPMC (160 g, Pharmacoat® 603) were granulated in a high speed mixer granulator. The wet granules were passed through a 9.4 mm sieve (Comil) before drying in a fluid bed dryer at an inlet air temperature of about 80° C. until the product temperature reached 42° C. The dry granules were sieved using a 1.6 mm grater sieve.

The dry granules were blended with microcrystalline cellulose (Avicel® pH 102) and sodium starch glycolate (Explotab®) in an 80 L drum for about 20 minutes at 28 rpm. Magnesium stearate and colloidal silicon dioxide (Aerosil® 200) were both individually pre-blended with about 500 g of the of the mixture of mesalazine granules, microcrystalline cellulose and sodium starch glycolate and passed through a 1 mm sieve before adding to the remainder of the mixture. The mixture was blended for about 5 minutes at 28 rpm to form a final compression blend.

Compression of the final compression blend was performed using a Fette P1200 tableting machine combined with an external lubrication system (PKB). Magnesium stearate was sprayed onto the punches of the tableting machine at a dose of 400 g/h.

The obtained capsules and tablet cores were coated as discussed below in Examples 1 to 3 and Comparative Examples 1 to 9.

Example 1 (5-ASA Capsule Cores Coated with Single Layer of a 70:30 Mixture of Eudragit® S 100 and High Amylose Starch; Aqueous Coating Preparation Containing 5% GMS and Polysorbate 80)

The coating was applied from a mixture of an aqueous starch dispersion (first aqueous preparation) and an aqueous Eudragit® S 100 dispersion (second aqueous preparation).

The aqueous starch dispersion was prepared by dispersing maize starch into butan-1-ol, followed by water, under magnetic stirring. The ratio of maize starch:butan-1-ol:water was 1:1:12.5. The resulting dispersion was heated to boiling and then cooled under stirring overnight.

The aqueous Eudragit® S 100 dispersion was prepared by dispersing Eudragit® S 100 in water under high speed stirring followed by partial (15-20%) neutralization with 1N ammonia solution (obtained by dilution of 25% ammonia solution).

The aqueous Eudragit® S 100 dispersion was added dropwise to the starch dispersion to obtain a ratio of Eudragit® S 100:starch of 70:30. The mixture was stirred for 1 hour and 60% TEC (based on Eudragit® S 100 polymer weight) and 5% glyceryl monostearate (GMS, based on Eudragit® S 100 polymer weight) were added and mixed for further 1 hour. An aqueous suspension of 13.18% iron oxide red (based on Eudragit® S 100 polymer weight) and 2.27% iron oxide yellow (based on Eudragit® S 100 polymer weight) was added and the mixture was mixed for further 10 minutes to form an outer layer coating preparation.

The GMS was added in the form of an emulsion prepared at a concentration of 5% w/w. Polysorbate 80 (40% based on GMS weight) was dissolved in distilled water followed by dispersion of the GMS. This dispersion was then heated to 75° C. for 15 minutes under strong magnetic stirring in order to form an emulsion. The emulsion was cooled at room temperature and under stirring.

The pigment suspension was formed by suspending red and yellow iron oxide pigments in water for 10 minutes under homogenization.

The outer layer coating preparation was sprayed on to the gelatin banded 5-ASA capsule cores using a pan coater, until a coating amount of 5 mg/cm² of Eudragit® S 100 was obtained.

The spray coating parameters were as follows: spraying rate 2.5-3.4 g/min; spray pressure 0.4 bar; pattern pressure 0.4 bar; air flow 40 m³/h; inlet air temperature 54-60° C.; outlet air temperature 41.4-42.5° C.; product temperature 29.5-41° C.; drum speed 10-14 rpm.

Example 2 (5-ASA Capsule Cores Coated with a Single Layer of a 50:50 Mixture of Eudragit® S 100 and High Amylose Starch; Aqueous Coating Preparation Containing 10% GMS and Polysorbate 80)

The coating was applied from a mixture of an aqueous starch dispersion (first aqueous preparation) and an aqueous Eudragit® S 100 dispersion (second aqueous preparation) using the same method as described for Example 1 with 10% GMS (based on Eudragit® S 100 polymer weight).

The aqueous Eudragit® S 100 dispersion was added dropwise to the starch dispersion to obtain a ratio of Eudragit® S 100:starch of 50:50.

The outer layer coating preparation was sprayed on to the gelatin banded 5-ASA capsule cores using a pan coater, until a coating amount of 5 mg/cm² of Eudragit® S 100 was obtained.

The spray coating parameters were as described for Example 1.

Example 3 (1600 mg 5-ASA Tablet Cores Coated with an HMPC Isolation Layer and an Outer Layer of a 70:30 Mixture of Eudragit® S 100 and High Amylose Starch; Aqueous Coating Preparation Containing 5% GMS, Based on Eudragit S® 100 and Polysorbate)

Isolation Layer

The isolation layer was applied from an aqueous mixture of HPMC and 20% PEG 6000.

The HPMC was dissolved in water under magnetic stirring and then the PEG 600 was added to form an isolation layer coating preparation. The isolation layer coating preparation was sprayed on to the 5-ASA tablet cores using a pan coater, until the coating amount of HPMC reached 3 mg/cm², to form isolation layer coated tablet cores.

Outer Layer

The outer layer coating was applied from a mixture of an aqueous starch dispersion (first aqueous preparation) and an aqueous Eudragit® S 100 dispersion (second aqueous preparation) prepared according to Example 1.

The outer layer coating preparation was sprayed on to the isolation layer coated 5-ASA tablet cores using a pan coater, until a coating amount of 5 mg/cm² of Eudragit® S 100 was obtained.

The spray coating parameters were as follows: spraying rate 2.0-2.8 g/min; spray pressure 0.4 bar; pattern pressure 0.5 bar; air flow 40 m³/h; inlet air temperature 52-60° C.; outlet air temperature 40.0-45.0° C.; product temperature 32.0-36.0° C.; drum speed 10-12 rpm.

Comparative Example 1 (5-ASA Capsule Cores Coated with a Single Layer of a 70:30 Mixture of Eudragit® S 100 and High Amylose Starch; "Semi-Organic" Coating Preparation Containing 5% GMS, Based on Eudragit® S 100 and Polysorbate)

The coating was applied from a mixture of an aqueous starch dispersion and an organic Eudragit® S 100 solution.

The aqueous starch dispersion was prepared by dispersing maize starch into butan-1-ol, followed by water, under magnetic stirring. The ratio of maize starch:butan-1-ol:water was 1:2:25. The resulting dispersion was heated to boiling and then cooled under stirring overnight.

The organic Eudragit® S 100 solution was prepared by dissolving Eudragit® S 100 in 96% ethanol under high speed stirring.

The starch dispersion was added dropwise to the Eudragit® S 100 solution to obtain a ratio of Eudragit® S 100:starch: of 70:30. The mixture was stirred for 1 hour and 29% TEC (based on Eudragit® S 100 polymer weight) and 5% glyceryl monostearate (GMS, based on Eudragit® S 100 polymer weight) were added and mixed for further 1 hour. A suspension of 13.18% iron oxide red (based on Eudragit® S polymer weight) and 2.27% iron oxide yellow (based on Eudragit® S 100 polymer weight) in ethanol was added and the mixture was mixed for further 10 minutes to form an outer layer coating preparation.

The GMS was added in the form of an emulsion as prepared in Example 1.

The outer layer coating preparation was sprayed on to the gelatin banded 5-ASA capsule cores using a pan coater, until a coating amount of 5 mg/cm² of Eudragit® S 100 was obtained.

The spray coating parameters were as described for Example 1.

Comparative Example 2 (5-ASA Capsule Cores Coated with Single Layer of a 70:30 Mixture of Eudragit® S 100 and High Amylose Starch; Aqueous Coating Preparation Containing 50% Talc)

The coating was applied from a mixture of an aqueous starch dispersion and an aqueous Eudragit® S 100 dispersion using the same method as described for Example 1, with talc (50% based on total Eudragit® S 100 polymer weight) as the anti-tack agent instead of GMS.

The talc was added in the form an aqueous suspension with the red and yellow iron oxide pigments.

The outer layer coating preparation was sprayed on to the isolation layer coated 5-ASA capsules using a pan coater, until a coating amount of 5 mg/cm$^2$ of Eudragit® S 100 was obtained.

The spray coating parameters were as described for Example 1.

Comparative Example 3 (1600 mg 5-ASA Tablet Cores Coated with a HPMC Isolation Layer and an Outer Layer of a 70:30 Mixture of Eudragit® S 100 and High Amylose Starch; "Semi-Organic" Coating Preparation Containing 5% GMS and Polysorbate)

Isolation Layer

The isolation layer was prepared and applied to the 5-ASA tablet cores according to Example 3.

Outer Layer

The outer layer coating was applied from a mixture of an aqueous starch dispersion and an organic Eudragit® S 100 solution as described for Comparative Example 1.

The outer layer coating preparation was sprayed on to the isolation layer coated 5-ASA tablet cores using a pan coater, until a coating amount of 5 mg/cm$^2$ of Eudragit® S 100 was obtained.

The spray coating parameters were as described for Example 3.

Comparative Example 4 (1600 mg 5-ASA Tablet Cores Coated with a HPMC Isolation Layer and an Outer Layer of a 70:30 Mixture of Eudragit® S 100 and High Amylose Starch; "Semi-Organic" Coating Preparation Containing 50% Talc)

The outer layer coating was applied from a mixture of an aqueous starch dispersion and an organic Eudragit® S 100 solution using the same method as described for Comparative Example 1, with talc (50% based on Eudragit® S 100 polymer weight) as the anti-tack agent instead of GMS.

The talc was added as an ethanolic suspension with the red and yellow iron oxide pigments.

The outer layer coating preparation was sprayed on to isolation layer coated 5-ASA tablet cores previously using a pan coater, until a coating amount of 5 mg/cm$^2$ of Eudragit® S 100 was obtained.

The spray coating parameters were as described for Example 3.

Comparative Example 5 (1600 mg 5-ASA Tablet Cores Coated with a HPMC Isolation Layer and an Outer Layer of a 70:30 Mixture of Eudragit® S 100 and High Amylose Starch; "Aqueous" Coating Preparation Containing 50% Talc)

Isolation Layer

The isolation layer was prepared and applied to the 5-ASA tablet cores according to Example 3.

Outer Layer

The outer layer coating was applied from a mixture of an aqueous starch dispersion and an aqueous Eudragit® S 100 dispersion as described for Comparative Example 2.

The outer layer coating preparation was sprayed on to the isolation layer coated 5-ASA tablet cores using a pan coater, until a coating amount of 5 mg/cm$^2$ of Eudragit® S 100 was obtained.

The spray coating parameters were as described for Example 1.

Comparative Example 6 (1600 mg 5-ASA Tablet Cores Coated with a HPMC Isolation Layer and an Outer Layer of a 70:30 Mixture of Eudragit® S 100 and High Amylose Starch; "Aqueous" Coating Preparation Containing 5% Talc)

Isolation Layer

The isolation layer was prepared and applied to the 5-ASA tablet cores according to Example 3.

Outer Layer

The outer layer coating was applied from a mixture of an aqueous starch dispersion and an aqueous Eudragit® S 100 dispersion as described for Comparative Example 2 with talc (5% based on Eudragit® S 100 polymer weight) as the anti-tack agent.

The outer layer coating preparation was sprayed on to the isolation layer coated 5-ASA tablet cores using a pan coater, until a coating amount of 5 mg/cm$^2$ of Eudragit® S 100 was obtained.

The spray coating parameters were as described for Example 1.

Comparative Example 7 (1600 mg 5-ASA Tablet Cores Coated with a HPMC Isolation Layer and an Outer Layer of a 70:30 Mixture of Eudragit® S 100 and High Amylose Starch; "Aqueous" Coating Preparation Containing 5% Talc and Polysorbate 80)

Isolation Layer

The isolation layer was prepared and applied to the 5-ASA tablet cores according to Example 3.

Outer Layer

The outer layer coating was applied from a mixture of an aqueous starch dispersion and an aqueous Eudragit® S 100 dispersion using the same method as described for Comparative Example 2, with talc (5% based on total Eudragit® S 100 solid content) as the anti-tack agent.

The talc was added in the form an aqueous dispersion with Polysorbate 80 (40% based on talc weight).

The outer layer coating preparation was sprayed on to the isolation layer coated 5-ASA tablet cores using a pan coater, until a coating amount of 5 mg/cm$^2$ of Eudragit® S 100 was obtained.

The spray coating parameters were as described for Example 1.

Comparative Example 8 (1600 mg 5-ASA Tablet Cores Coated with a HPMC Isolation Layer and an Outer Layer of a 70:30 Mixture of Eudragit® S 100 and High Amylose Starch; "Aqueous" Coating Preparation Containing 5% Colloidal Silicon Dioxide)

Isolation Layer

The isolation layer was prepared and applied to the 5-ASA tablet cores according to Example 3.

Outer Layer

The outer layer coating was applied from a mixture of an aqueous starch dispersion and an aqueous Eudragit® S 100 dispersion as described for Comparative Example 2 with 5% colloidal silicon dioxide (Aerosil® 300) as the anti-tack agent.

The colloidal silica (Aerosil® 300) was added in the form a dispersion. Aerosil 300 (5%, based on total Eudragit® S 100 polymer weight) was homogenized in water for 10 minutes and then added to the mixture of the aqueous starch dispersion and the aqueous Eudragit® S 100 dispersion.

The outer layer coating preparation was sprayed on to the isolation layer coated 5-ASA tablet cores using a pan coater, until a coating amount of 5 mg/cm² of Eudragit® S 100 was obtained.

The spray coating parameters were as described for Example 1.

Comparative Example 9 (1600 mg 5-ASA Tablet Cores Coated with a HPMC Isolation and an Outer Layer of a 70:30 Mixture of Eudragit® S 100 and High Amylose Starch; "Aqueous" Coating Preparation Containing 5% Colloidal Silicon Dioxide)

Isolation Layer

The isolation layer was prepared and applied to the 5-ASA tablet cores according to Example 3.

Outer Layer

The outer layer coating was applied from a mixture of an aqueous starch dispersion and an aqueous Eudragit® S 100 dispersion as described for Comparative Example 2 with 5% colloidal silicon dioxide (Syloid 244 FP) as the anti-tack agent.

The colloidal silica (Syloid 244 FP) was added in the form a dispersion. Syloid 244 FP (5%, based on total Eudragit® S 100 polymer weight) was homogenized in water for 10 minutes and then added to the mixture of the aqueous starch dispersion and the aqueous Eudragit® S 100 dispersion.

The outer layer coating preparation was applied to the isolation layer coated 5-ASA tablet cores using a pan coater, until a coating amount of 5 mg/cm² of Eudragit® S 100 was obtained.

The spray coating parameters were as described for Example 3.

Acid Resistance Test

Acid resistance testing was performed using a disintegration apparatus and basked rack assembly. 6 coated tablets or capsules were tested in 0.1 M HCl for 2 hours at 37° C. Tablets and capsules were considered acid resistant if no visible cracks or deformation of the coating was observed.

Acid resistance of coated tablets was also determined after mechanical stress. 6 tablets were subjected to 100 rotations (25 rpm/4 minutes) in a friability tester, prior to being tested in 0.1 M HCl for 2 hours at 37° C.

Drug Release Test #1—Simulated Fasted State then Dissolution in Hanks Buffer at pH 6.8

In vitro dissolution studies were performed on a USP type II apparatus using a paddle speed of 50 rpm and a media temperature of 37±0.5° C. To simulate the "fasted" state, capsules/tablets were first tested in 0.1 M HCl for 2 hours followed by 10 hours in Hanks buffer (pH 6.8).

The pH of the buffer was stabilized at 6.8±0.05 by continuously sparging with 5% $CO_2$/95% $O_2$. Absorbance measurements were taken at 5 minute intervals, with an absorbance wavelength of 301 nm in HCl and 330 nm in Hanks buffer (pH 6.8).

Drug Release Test #2—Simulated Fasted State then Dissolution in Krebs Buffer at pH 7.4

In vitro dissolution studies were performed on a USP type II apparatus using a paddle speed of 50 rpm and a media temperature of 37±0.5° C.

To simulate the "fasted" state, tablets/capsules were first tested in 0.1 M HCl for 2 hours followed by 10 hours in Krebs buffer (pH 7.4).

Drug Release Test #3—Simulated Fasted State then Dissolution in SøRenson Buffer at pH 6.8

In vitro dissolution studies were performed on a USP type II apparatus using a paddle speed of 50 rpm and a media temperature of 37±0.5° C. The coated capsules/tablets were tested in Sørenson buffer at pH 6.8 (35.4 mM $KH_2PO_4$+35.6 mM $NaH_2PO_4$).

To simulate the "fasted" state, capsules/tablets were first tested in 0.1 M HCl for 2 hours using a disintegration apparatus followed by 18 hours in Sørenson buffer (pH 6.8).

Drug Release Test #4—Simulated Fasted State then Dissolution in SøRenson Buffer at pH 6.8 with 50 U/mL α-Amylase (Effect of α-Amylase Triggered Release).

In vitro dissolution studies were performed on a USP type II apparatus using a paddle speed of 50 rpm and a media temperature of 37±0.5° C. The coated capsules/tablets were tested in Sørenson buffer at pH 6.8 (35.4 mM $KH_2PO_4$+35.6 mM $NaH_2PO_4$) containing 50 U (units)/ml α-amylase derived from *B. licheniformis*.

To simulate the "fasted" state, capsules/tablets were first tested in 0.1 M HCl for 2 hours using a disintegration apparatus followed by 18 hours in Sørenson buffer (pH 6.8).

Results

Coated Capsules

The results presented in FIGS. 1 to 3 demonstrate that the coated capsules prepared according to the method of the present invention have improved dissolution properties when compared to the coated capsules of the Comparative Examples.

In gastric simulated fluid, all coated capsules tested were robust for at least 2 hours, independent of the coating composition. In addition, in aqueous solution at pH 6.8 (data not shown), no release of 5-ASA was observed from any of the capsules tested in the 10 hours that the capsules were exposed to simulated conditions of the small intestine (drug release test #1, Hank's buffer, pH 6.8). Notably, the preparation of the outer coating using an aqueous coating preparation resulted in coated capsules which were resistant to simulated small intestinal conditions, independent of the starch ratio (Example 1 and 2) and independent of the anti-tack agent used, i.e. GMS (Example 1 and Example 2) and talc (Comparative Example 2).

However, it should be noted that once the capsules were exposed to pH 7.4 (drug release test #2, FIG. 1), initial release of 5-ASA from coated capsules prepared according to the method of the present invention occurred earlier than for Comparative Example 1 capsules (which were prepared using a conventional "semi-organic" coating preparation). Notably, increasing the starch content of the coating did not significantly change the dissolution profile under these conditions (FIG. 1, compare Examples 1 and 2). Replacing GMS with talc as the anti-tack agent resulted in a delay in the initial release of 5-ASA (FIG. 1, compare Example 1 and Comparative Example 2).

Enzymatic Digestion

In aqueous solution at pH 6.8, enzymatic triggered release was observed for the coated capsules of Examples 1 and 2 (drug release tests #3 and #4, FIG. 2). Specifically, initial release of 5-ASA was observed when α-amylase was present in the buffer solution at pH 6.8. This is consistent with WO2013/164315A in which it was found that the presence of starch in the outer layer enables release of a significant amount of the active when exposed to colonic enzymes even though the pH of the surrounding medium is well below the pH threshold of the second polymeric material. This result also demonstrates that the presence of colonic enzymes in the surrounding medium is necessary to achieve significant release of the active under these conditions, thereby efficiently preventing premature drug release.

Increasing the starch content of the coating did not significantly change the dissolution profile under these conditions.

In contrast, whilst enzymatic triggered release was observed for the capsules of Comparative Example 1 (which were prepared using a conventional "semi-organic" outer coating preparation), the release was triggered later than for the coated capsules of Examples 1 and 2 according to the present invention. Without being bound by any particular theory, the Inventors believe that this may be explained by a tighter film structure when the coating is prepared from a "semi-organic" coating preparation.

The Inventors have also observed that replacing GMS with talc as the anti-tack agent results in a higher variability in coating dissolution and eliminates the enzymatic triggered release from the capsules thereby compromising the drug release mechanism when the pH is below the pH at which the enteric polymer dissolves (FIG. 3, Comparative Example 2). Therefore, coatings comprising GMS as the anti-tack agent are superior to those containing talc as the anti-tack agent. In addition, since talc is a less effective anti-tack agent than GMS, it is necessary to use it in in higher quantities than GMS (50 wt % talc based on Eudragit® S 100 versus 10 wt % GMS). This means that the amount of excipients in the coating is significantly higher, which could potentially hinder amylase accessibility to the starch embedded in the film matrix.

Coated Tablets

The coatings were applied to the 1600 mg 5-ASA tablets coated with a HPMC isolation layer without any processing difficulties. The results presented in Table 1 and FIGS. 4 and 5 demonstrate that the coated tablets prepared according to the method of the present invention have improved gastric resistance as well as gastric resistance after mechanical impact (Example 3) and improved dissolution properties when compared to the coated tablets of the Comparative Examples.

In gastric simulated fluid (0.1 M HCl for 2 hours), the coated tablets of both Example 3 and Comparative Example 3 (both of which use GMS as the anti-tack agent) were robust for at least 2 hours. Thus, the use GMS as the anti-tack agent in the outer coating layer produces coated tablets which are gastric resistant, independent of whether an aqueous or a semi-organic coating preparation is used to prepare the outer layer.

Coated tablets of Comparative Example 5 to Comparative Example 9 (all of which use inorganic anti-tack agents) were not sufficiently robust in simulated gastric fluid leading to premature release of 5-ASA.

In addition, the coated tablets of Example 3 demonstrated 100% acid resistance even after mechanical impact. In contrast, the coated tablets of Comparative Examples 5 to 9 demonstrated very poor acid resistance after mechanical impact.

TABLE 1

| Examples | Anti-tack agent | | Outer layer coating preparation | Acid resistance (%) | Acid resistance after mechanical impact (%) |
| --- | --- | --- | --- | --- | --- |
| | Type | Quantity (%) | | | |
| Example 3 | GMS | 5 | Aqueous | 100 | 100 |
| Comparative Example 3 | GMS | 5 | Semi-organic | 100 | 100 |
| Comparative Example 4 | Talc | 50 | Semi-organic | 83.33 | 83.33 |
| Comparative Example 5 | Talc | 50 | Aqueous | 83.33 | 33.33 |
| Comparative Example 6 | Talc | 5 | Aqueous | 33.33 | 16.67 |
| Comparative Example 7 | Talc | 5 | Aqueous | 33.33 | 0.00 |
| Comparative Example 8 | Aerosil® 300 | 5 | Aqueous | 0 | 0 |
| Comparative Example 9 | Syloid 244 FP | 5 | Aqueous | 0 | 0 |

When the coated tablets were tested in vitro for drug release in pH 6.8 Hanks buffer to simulate the conditions of the proximal small intestine, after exposure to simulated gastric conditions (drug release test #1), higher resistance to dissolution was observed for the coated tablets of Example 3 comprising 5% GMS in the outer coating than for the tablets of Comparative Example 5 comprising talc in the outer coating (FIG. 4). In particular, release of 5-ASA from the tablets of Example 3 was well below 5% after 10 hours whereas the coated tablets of Comparative Example 5 showed around 30% release of 5-ASA after 10 hours.

Additionally, upon exposure to pH 7.4 Krebs buffer (drug release test #2) to simulate the conditions of the ileo-colonic region, rapid pH triggered release of 5-ASA was observed for the coated tablets of Example 3 containing 5% GMS (FIG. 5) in the outer coating, indicating that once the pH trigger of the enteric polymer is reached (pH above 7), rapid coating dissolution and drug release occurs. Replacing GMS with talc as the anti-tack agent (Comparative Example 5) resulted in a delay in the initial release of 5-ASA, slower dissolution of the coating and therefore slower release of 5-ASA (FIG. 5).

Thus, it can be seen that the combination of an organic anti-tack agent and an aqueous outer coating preparation produces delayed release formulations that are superior to comparative formulations.

It will be appreciated that the invention is not restricted to the details described above with reference to the preferred embodiments but that numerous modifications and variations can be made without departing from the scope of the invention.

The invention claimed is:

1. A method of producing a delayed release drug formulation for oral administration to deliver a drug to the colon, said method comprising:
   forming a core comprising a drug;
   combining a first aqueous preparation of an enzymatically degradable polysaccharide which is degradable by colonic bacterial enzymes; a second aqueous preparation of a film-forming enteric polymer having a pH threshold of about pH 6 or above; and an organic anti-tack agent, to form an outer layer coating preparation; and
   coating the core with the outer layer coating preparation to form an outer layer coated core,
   wherein the proportion of the enzymatically degradable polysaccharide to the film-forming enteric polymer in the outer coating preparation is in a range from 10:90 to 50:50, and
   wherein the outer layer coating preparation comprises no more than about 5% v/v organic solvent.

2. The method as claimed in claim 1, wherein the second aqueous preparation is formed by suspending the enteric polymer in water under stirring to form a suspension, and partially neutralising the suspension with a base.

3. The method as claimed in claim 2, wherein the base is added to the suspension in an amount sufficient to neutralise from about 10% to about 30% of carboxylic acid groups in the enteric polymer.

4. The method as claimed in claim 2, wherein the suspension is partially neutralised using aqueous ammonia.

5. The method as claimed in claim 4, wherein the aqueous ammonia has a concentration from about 0.5 N to about 2 N.

6. The method as claimed in claim 1, wherein the organic anti-tack agent is in the form of an aqueous dispersion.

7. The method as claimed in claim 6, wherein the aqueous dispersion comprises a surfactant.

8. The method as claimed in claim 7, wherein the surfactant is non-ionic.

9. The method as claimed in claim 7, wherein the surfactant is hydrophilic.

10. The method as claimed in claim 1, wherein the organic anti-tack agent is glyceryl monostearate (GMS) or stearic acid.

11. The method as claimed in claim 1, wherein the core is pre-coated with an isolation layer comprising a film-forming non-ionic polymer that is soluble in gastrointestinal fluid, an inner layer comprising a polymeric material which is soluble in intestinal or gastrointestinal fluid, or both the isolation layer and the inner layer;
   wherein said polymeric material is selected from the group consisting of a polycarboxylic acid polymer that is at least partially neutralised, and a non-ionic polymer,
   provided that, where said polymeric material is a non-ionic polymer, said inner layer comprises at least one additive selected from a buffer agent and a base.

12. The method as claimed in claim 11, wherein the inner layer, when present, comprises a buffer agent and a base.

13. A delayed release drug formulation for oral administration to deliver a drug to the colon, said formulation produced according to the method of claim 1, comprising:
   a core comprising a drug, and
   an outer coating layer for the core, the outer coating layer comprising a mixture of an enzymatically degradable polysaccharide which is degradable by colonic bacterial enzymes, a film-forming enteric polymer having a pH threshold at about pH 6 or above, and an organic anti-tack agent;
   wherein the outer coating layer comprises no more than about 5000 ppm residual free organic solvent; and,
   wherein the proportion of the enzymatically degradable polysaccharide to the film-forming enteric polymer in the outer coating preparation is in a range from 10:90 to 50:50.

14. The delayed release drug formulation according to claim 13, comprising an inner layer located between said core and said outer coating layer, wherein said inner layer comprises a film-forming non-ionic polymer that is soluble in gastrointestinal fluid, a buffer agent, and a base.

15. The delayed release drug formulation according to claim 13, comprising an isolation layer located on the surface of the core, said isolation layer comprising a film-forming non-ionic polymer that is soluble in gastrointestinal fluid.

16. The method as claimed in claim 3, wherein the base is added to the suspension in an amount sufficient to neutralise from about 15% to 20% of carboxylic acid groups in the enteric polymer.

17. The method as claimed in claim 5, wherein the aqueous ammonia has a concentration of about 1 N.

18. The delayed release drug formulation according to claim 13, wherein the outer coating layer comprises at least 10% by weight of at least one plasticizer based on the weight of the film-forming enteric polymer.

19. The delayed release drug formulation according to claim 13, wherein the outer coating layer comprises at least 40% by weight of at least one plasticizer based on the weight of the film-forming enteric polymer.

20. A delayed release drug formulation for oral administration to deliver a drug to the colon, said formulation comprising:
   a core comprising a drug, and
   an outer coating layer for the core, the outer coating layer comprising a mixture of an enzymatically degradable polysaccharide which is degradable by colonic bacterial enzymes, a film-forming enteric polymer having a pH threshold at pH 6 or above, and an organic anti-tack agent;
   wherein the outer coating layer comprises at least 50% by weight of at least one plasticiser based on the weight of the film-forming enteric polymer.

* * * * *